US012607622B2

(12) United States Patent
Foster et al.

(10) Patent No.: US 12,607,622 B2
(45) Date of Patent: Apr. 21, 2026

(54) METHOD FOR DIAGNOSING AND MONITORING INFLAMMATORY DISEASE PROGRESSION

(71) Applicants: MCMASTER UNIVERSITY, Hamilton (CA); The Regents of the University of California, Oakland, CA (US)

(72) Inventors: Warren Foster, Ancaster (CA); Jocelyn Wessels, Guelph (CA); Sanjay Agarwal, Rancho Santa Fe, CA (US); Leyla Soleymani, Oakville (CA)

(73) Assignees: The Regents of the University of California, Oakland, CA (US); MCMASTER UNIVERSITY, Hamilton (CA)

( * ) Notice: Subject to any disclaimer, the term of this patent is extended or adjusted under 35 U.S.C. 154(b) by 1080 days.

(21) Appl. No.: 17/545,041

(22) Filed: Dec. 8, 2021

(65) Prior Publication Data
US 2022/0326222 A1     Oct. 13, 2022

Related U.S. Application Data

(63) Continuation of application No. 15/632,497, filed on Jun. 26, 2017, now Pat. No. 11,221,327, which is a continuation-in-part of application No. 15/094,086, filed on Apr. 8, 2016, now Pat. No. 10,415,093, which is a continuation-in-part of application No. PCT/CA2014/000742, filed on Oct. 10, 2014.

(60) Provisional application No. 61/889,085, filed on Oct. 10, 2013.

(51) Int. Cl.

| | |
|---|---|
| *G01N 33/50* | (2006.01) |
| *B01L 3/00* | (2006.01) |
| *C07K 16/22* | (2006.01) |
| *C12Q 1/6883* | (2018.01) |
| *G01N 33/53* | (2006.01) |
| *G01N 33/68* | (2006.01) |
| *G01N 33/74* | (2006.01) |

(52) U.S. Cl.
CPC ........ *G01N 33/5023* (2013.01); *B01L 3/5023* (2013.01); *C07K 16/22* (2013.01); *C12Q 1/6883* (2013.01); *G01N 33/53* (2013.01); *G01N 33/689* (2013.01); *G01N 33/74* (2013.01); *B01L 2300/0819* (2013.01); *C12Q 2600/118* (2013.01); *C12Q 2600/158* (2013.01); *G01N 2333/475* (2013.01); *G01N 2800/364* (2013.01); *G01N 2800/52* (2013.01)

(58) Field of Classification Search
CPC ..... C12Q 1/68; C12Q 2600/158; G01N 33/53
See application file for complete search history.

(56) References Cited

U.S. PATENT DOCUMENTS

| | | |
|---|---|---|
| 2006/0014166 A1 | 1/2006 | Cohen et al. |
| 2012/0220034 A1 | 8/2012 | Ahlfors et al. |

OTHER PUBLICATIONS

Borghese, et al. (2010) Gynecol Obstet Fertil. Jul-Aug. 38(7-8):442-6.
Browne, et al. (2012) Fertil Steril. Sep; 98(3):713-9.
Giannini, et al. (2010) J Endometr Pelvic Pain Disord 2(3): 144-150.
Ahern et al. (1995) The Scientist; 9(15):20.
Keeton, Biological Science, 2nd Ed. p. 250, Norton & Co. New York.
Bucci et al. (2011) J. Endometriosis; 3(1):40-46.
Desmet et al. (2006) Cell. Mol. Life Sci. 63:755-759.
Giannini et al. (2010) J. Endometriosis; 2(3):144-150.
Signorile et al. (2016) J. Cell. Physiol. 231:2622-2627.
Telimaa, et al. (1989) Am. J. Obstet. Gynecol. 161, 4, 866.
Wessels, et al. (2016) Fertility and Sterility; 105, 1, 119.
Office Action (2021) CA 2,926,372.

*Primary Examiner* — Ethan C Whisenant
(74) *Attorney, Agent, or Firm* — Milstein Zhang & Wu LLC

(57) ABSTRACT

Methods for diagnosing or monitoring endometriosis in a mammal are provided. The methods include the steps of determining the expression levels of BDNF, glycodelin and optionally ZAG, in a biological sample from the mammal, and determining that the mammal has endometriosis when the biomarker expression levels in the sample are elevated.

15 Claims, 21 Drawing Sheets

Specification includes a Sequence Listing.

Circulating BDNF in Women With and Without Endometriosis

Circulating BDNF in Women With and Without Endometriosis by Stage of Disease

Plasma BDNF in Cases

Effect of Treatment on Circulating BDNF concentrations in Women With and Without Endometriosis

Relationship between Circulating BDNF Concentrations and Pain in Women with Untreated Endometriosis

Figure 6
Figure 6 Wessels et al., 2013
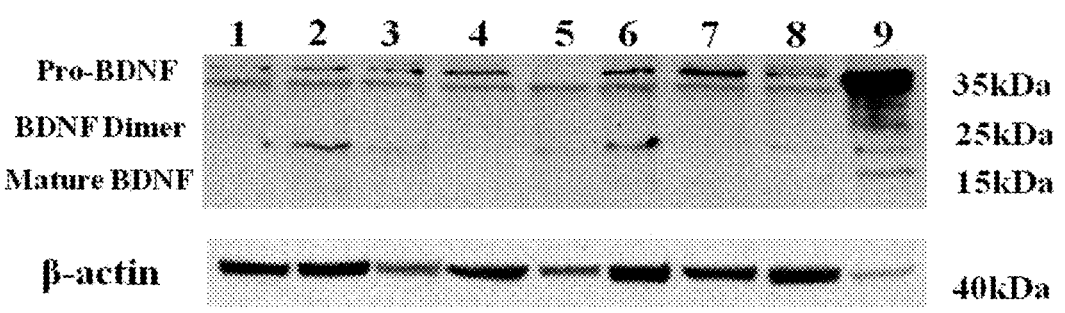
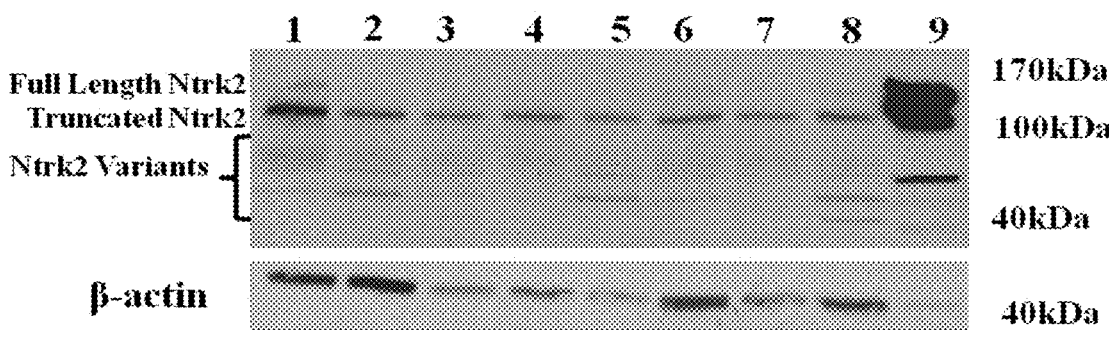

Figure 7

With Endometriosis                    Without Endometriosis 1          2          3          4          5          6          7

TrkB-FL

TrkB-T1/2

```
 1 AVDMSGGTVT VLEKVPVSKG QLKQYFYETK CNPMGYTKEG CRGIDKRHWN SQCRTTQSYV
61 RALTMDSKKR IG (SEQ ID NO:1)
```

*B*

```
 1 AVDMSGGTVT VLEKVPVSKG QLKQYFYETK CNPMGYTKEG CRGIDKRHWN SQCRTTQSYV
61 RALTMDSKKR IG (SEQ ID NO:1)
```

*C*

```
 1 AVDMSGGTVT VLEKVPVSKG QLKQYFYETK CNPMGYTKEG CRGIDKRHWN SQCRTTQSYV
61 RALTMDSKKR IG (SEQ ID NO:1)
```

*D*

```
 1 SITLSCSVAG DPVPNMYWDV GNLVSKHMNE TSHTQGSLRI TNISSDDSGK QISCVAENLV
61 GEDQDSVNLT (SEQ ID NO:2)
```

*E*

```
 1 KSVTLSCSVG GDPLPTLYWD VGNLVSKHMN ETSHTQGSLR ITNISSDDSG KQISCVAENL
61 VGEDQDSVNL T (SEQ ID NO:3)
```

*F*

```
 1 SVTISCSVGG DPLPTLYWDV GNLVSKHMNE TSHTQGSLRI TNISSDDSGK QISCVAENLV
61 GEDQDSVNLT (SEQ ID NO:4)
```

```
  1 tgcagtggac atgtcgggcg ggacggtcac agtccttgaa aaggtccctg tatcaaaagg
 61 ccaactgaag caatacttct acgagaccaa gtgcaatccc atgggttaca caaaagaagg
121 ctgcaggggc atagacaaaa ggcattggaa ctcccagtgc cgaactaccc agtcgtacgt
181 gcgggccctt accatggata gcaaaaagag aattggctg (SEQ ID NO:5)
```

B

```
  1 tgcagtggac atgtctggcg ggacggtcac agtcctagag aaagtcccgg tatccaaagg
 61 ccaactgaag cagtatttct acgagaccaa gtgtaatccc atgggttaca ccaaggaagg
121 ctgcagggc atagacaaaa ggcactggaa ctcgcaatgc cgaactaccc aatcgtatgt
181 tcgggccctt actatggata gcaaaaagag aattgg (SEQ ID NO:6)
```

C

```
  1 tgcagtggac atgtccggtg ggacggtcac agtcctggag aaagtcccgg tatcaaaagg
 61 ccaactgaag caatatttct acgagaccaa gtgtaatccc atgggttaca cgaaggaagg
121 ctgcagggc atagacaaaa ggcactggaa ctcgcaatgc cgaactaccc aatcgtatgt
181 tcgggccctt actatggata gcaaaaagag aattggctg (SEQ ID NO:7)
```

D

```
  1 gtctatcaca ttatcctgta gtgtggcagg tgatccggtt cctaatatgt attgggatgt
 61 tggtaacctg gtttccaaac atatgaatga aacaagccac acacagggct ccttaaggat
121 aactaacatt tcatccgatg acagtgggaa gcagatctct tgtgtggcgg aaaatcttgt
181 aggagaagat caagattctg tcaacctcac (SEQ ID NO:8)
```

E

```
  1 tgcagtggac atgtctggcg ggacggtcac agtcctagag aaagtcccgg tatccaaagg
 61 ccaactgaag cagtatttct acgagaccaa gtgtaatccc atgggttaca ccaaggaagg
121 ctgcagggc atagacaaaa ggcactggaa ctcgcaatgc cgaactaccc aatcgtatgt
181 tcgggccctt actatggata gcaaaaagag aattgg (SEQ ID NO:6)
```

F

```
  1 tgcagtggac atgtccggtg ggacggtcac agtcctggag aaagtcccgg tatcaaaagg
 61 ccaactgaag caatatttct acgagaccaa gtgtaatccc atgggttaca cgaaggaagg
121 ctgcagggc atagacaaaa ggcactggaa ctcgcaatgc cgaactaccc aatcgtatgt
181 tcgggccctt actatggata gcaaaaagag aattggctg (SEQ ID NO:7)
```

```
  1 mlcllltlgv alvcgvpamd ipqtkqdlel pkaplrvhit sllptpednl eivlhrwenn
 61 scvekkvlge ktenpkkfki nytvaneatl ldtdydnflf lclqdtttpi qsmmcqylar
121 vlveddeimq gfirafrplp rhlwylldlk qmeepcrf (SEQ ID NO: 13)
```

B)

```
  1 mlcllltlgv alvcgvpamd ipqtkqdlel pklagtwhsm amatnnislm atlkaplrvh
 61 itsllptped nleivlhrwe nnscvekkvl gektenpkkf kinytvanea tlldtdydnf
121 lflclqdttt piqsmmcqyl arvlveddei mqgfirafrp lprhlwylld lkqmeepcrf
    (SEQ ID NO: 14)
```

C)

```
  1 mlcllltlgv alvcgvpamd ipqtkqdlel pklagtwhsm amatnnislm atlkaplrvh
 61 itsllptped nleivlhrwe nnscvekkvl gektenpkkf kinytvanea tlldtdydnf
121 lflclqdttt piqsmmcqyl arvlveddei mqgfirafrp lprhlwylld lkqmeepcrf
    (SEQ ID NO: 15)
```

```
  1 agcatccctc tggctccaga gctcagagcc acccacagcc gcagccatgc tgtgcctcct
 61 gctcaccctg ggcgtggccc tggtctgtgg tgtcccggcc atggacatcc cccagaccaa
121 gcaggacctg gagctcccaa agttggcagg gacctggcac tccatggcca tggcgaccaa
181 caacatctcc ctcatggcga cactgaaggc ccctctgagg gtccacatca cctcactgtt
241 gcccaccccc gaggacaacc tggagatcgt tctgcacaga tgggagaaca acagctgtgt
301 tgagaagaag gtccttggag agaagactga gaatccaaag aagttcaaga tcaactatac
361 ggtggcgaac gaggccacgc tgctcgatac tgactacgac aatttcctgt ttctctgcct
421 acaggacacc accacccca tccagagcat gatgtgccag tacctggcca gagtcctggt
481 ggaggacgat gagatcatgc agggattcat cagggctttc aggcccctgc ccaggcacct
541 atggtacttg ctggacttga aacagatgga agagccgtgc cgtttctagc tcacctccgc
601 ctccaggaag accagactcc caccttcca cacctccaga gcagtgggac ttcctcctgc
661 cctttcaaag aataaccaca gctcagaaga cgatgacgtg gtcatctgtg tcgccatccc
721 cttcctgctg cacacctgca ccacggccat ggggaggctg ctccctgggg gcagagtctc
781 tggcagaggt tattaataaa cccttggagc atgaaaaaaa aaaaaaaaa
```
(SEQ ID NO: 16)

E)

```
  1 agcatccctc tggctccaga gctcagagcc acccacagcc gcagccatgc tgtgcctcct
 61 gctcaccctg ggcgtggccc tggtctgtgg tgtcccggcc atggacatcc cccagaccaa
121 gcaggacctg gagctcccaa agttggcagg gacctggcac tccatggcca tggcgaccaa
181 caacatctcc ctcatggcga cactgaaggc ccctctgagg gtccacatca cctcactgtt
241 gcccaccccc gaggacaacc tggagatcgt tctgcacaga tgggagaaca acagctgtgt
301 tgagaagaag gtccttggag agaagactga gaatccaaag aagttcaaga tcaactatac
361 ggtggcgaac gaggccacgc tgctcgatac tgactacgac aatttcctgt ttctctgcct
421 acaggacacc accacccca tccagagcat gatgtgccag tacctggcca gagtcctggt
481 ggaggacgat gagatcatgc agggattcat cagggctttc aggcccctgc ccaggcacct
541 atggtacttg ctggacttga aacagatgga agagccgtgc cgtttctagc tcacctccgc
601 ctccaggaag accagactcc caccttcca cacctccaga gcagtgggac ttcctcctgc
661 cctttcaaag aataaccaca gctcagaaga cgatgacgtg gtcatctgtg tcgccatccc
721 cttcctgctg cacacctgca ccacggccat ggggaggctg ctccctgggg gcagagtctc
781 tggcagaggt tattaataaa cccttggagc atgaaaaaaa aaaaaaaaa
```
(SEQ ID NO: 17)

F)

```
  1 agcatccctc tggctccaga gctcagagcc acccacagcc gcagccatgc tgtgcctcct
 61 gctcaccctg ggcgtggccc tggtctgtgg tgtcccggcc atggacatcc cccagaccaa
121 gcaggacctg gagctcccaa agttggcagg gacctggcac tccatggcca tggcgaccaa
181 caacatctcc ctcatggcga cactgaaggc ccctctgagg gtccacatca cctcactgtt
241 gcccaccccc gaggacaacc tggagatcgt tctgcacaga tgggagaaca acagctgtgt
301 tgagaagaag gtccttggag agaagactga gaatccaaag aagttcaaga tcaactatac
361 ggtggcgaac gaggccacgc tgctcgatac tgactacgac aatttcctgt ttctctgcct
421 acaggacacc accacccca tccagagcat gatgtgccag tacctggcca gagtcctggt
481 ggaggacgat gagatcatgc agggattcat cagggctttc aggcccctgc ccaggcacct
541 atggtacttg ctggacttga aacagatgga agagccgtgc cgtttctagg tgagctcctg
601 cctggtcctg cctcctggct cacctccgcc tccaggaaga ccagactccc acccttccac
661 acctccagag cagtgggact tcctcctgcc ctttcaaaga ataaccacag ctcagaagac
721 gatgacgtgg tcatctgtgt cgccatcccc ttcctgctgc acacctgcac cacggccatg
781 gggaggctgc tccctggggg cagagtctct ggcagaggtt attaataaac ccttggagca
841 tgaaaaaaaa aaaaaaaaa
```
(SEQ ID NO: 18)

```
  1 mvrmvpvlls lllllgpavp qenqdgrysl tyiytglskh vedvpafqal gslndlqffr
 61 ynskdrksqp mglwrqvegm edwkqdsqlq karedifmet lkdiveyynd sngshvlqgr
121 fgceiennrs sgafwkyyyd gkdyiefnke ipawvpfdpa aqitkqkwea epvyvqraka
181 yleeecpatl rkylkyskni idrqdppsvv vtshqapgek kklkclaydf ypgkidvhwt
241 ragevqepel rgdvlhngng tyqswvvvav ppqdtapysc hvqhsslaqp lvvpweas
    (SEQ ID NO: 19)
```

B)

```
   1 ccattggcct gtagattcac ctccctgggg cagggcccca ggacccagga taatatctgt
  61 gcctcctgcc cagaaccctc caagcagaca caatggtaag aatggtgcct gtcctgctgt
 121 ctctgctgct gcttctgggt cctgctgtcc cccaggagaa ccaagatggt cgttactctc
 181 tgacctatat ctacactggg ctgtccaagc atgttgaaga cgtccccgcg tttcaggccc
 241 ttggctcact caatgacctc cagttcttta gatacaacag taaagacagg aagtctcagc
 301 ccatgggact ctggagacag gtggaaggaa tggaggattg gaagcaggac agccaacttc
 361 agaaggccag ggaggacatc tttatggaga ccctgaaaga catcgtggag tattacaacg
 421 acagtaacgg gtctcacgta ttgcagggaa ggtttggttg tgagatcgag aataacagaa
 481 gcagcggagc attctggaaa tattactatg atggaaagga ctacattgaa ttcaacaaag
 541 aaatcccagc ctgggtcccc ttcgacccag cagcccagat aaccaagcag aagtgggagg
 601 cagaaccagt ctacgtgcag cgggccaagg cttacctgga ggaggagtgc cctgcgactc
 661 tgcggaaata cctgaaatac agcaaaaata tcctggaccg gcaagatcct ccctctgtgg
 721 tggtcaccag ccaccaggcc ccaggagaaa agaagaaact gaagtgcctg gcctacgact
 781 tctacccagg gaaaattgat gtgcactgga ctcgggccgg cgaggtgcag gagcctgagt
 841 tacggggaga tgttcttcac aatggaaatg gcacttacca gtcctgggtg gtggtggcag
 901 tgccccccgca ggacacagcc ccctactcct gccacgtgca gcacagcagc ctggcccagc
 961 ccctcgtggt gccctgggag gccagctagg aagcaagggt tggaggcaat gtgggatctc
1021 agacccagta gctgcccttc ctgcctgatg tgggagctga accacagaaa tcacagtcaa
1081 tggatccaca aggcctgagg agcagtgtgg ggggacagac aggaggtgga tttggagacc
1141 gaagactggg atgcctgtct tgagtagact tggacccaaa aaatcatctc accttgagcc
1201 cacccccacc ccattgtcta atctgtagaa gctaataaat aatcatccct ccttgcctag
1261 cataaaaaaa aaaaaaaa    (SEQ ID NO: 20)
```

C)

```
  1 mvpvllsipl llgpavfqet gsyyltflyt glsrpskgfp rfqataflnd qaffhynsns
 61 gkaepvgpws qvegmedwek esqlqraree iflvtlkdim dyykdttgsh tfqgmfgcei
121 tnnrssgavw ryaydgedfi efnkeipawi pldpaaantk lkweaekvyv qrakayleee
181 cpemlkryln ysrshldrid pptvtitsrv ipggnrifkc laygfypqri slhwnkankk
241 lafepergvf pngngtylsw aevevspqdi dpffclidhr gfsqslsvqw drtrkvkden
301 nvvaqpq (SEQ ID NO: 21)
```

```
   1 tttcctgtgt agactgttct cccgggcact accgtagcaa tggtgcctgt cctgctgtcc
  61 ctgcctctcc ttctgggtcc tgcagtcttt caggagactg ggtcttatta tctgaccttt
 121 ctctacaccg ggttgtccag acccagcaaa ggttttccga ggtttcaagc cactgcattt
 181 ctcaatgacc aggccttctt ccactacaac agcaacagcg ggaaggcaga gcctgtggga
 241 ccttggagcc aggtggaagg aatggaggac tgggagaagg aaagccagct tcagagggcc
 301 agggaggaga tcttccttgt gaccctgaaa gacatcatgg actattacaa ggacactaca
 361 gggtctcaca cctttcaggg aatgtttggt tgcgagatca caaataacag aagtagtgga
 421 gctgtctgga ggtatgccta cgacggagag gatttcatcg aattcaacaa agaaatccca
 481 gcttggatcc ccttagaccc agcagctgca aacaccaagc taaagtggga agcagaaaag
 541 gtctacgtgc agcgagccaa ggcataccta gaggaggagt gtcctgaaat gctgaagagg
 601 tacctgaact acagtcgatc tcacctggac cgaatagatc ctcccactgt gacaatcacc
 661 agccgtgtga tcccaggagg aaacagaata ttcaaatgcc tggcctatgg cttctaccca
 721 caaagaatta gtctgcactg gaacaaggcc aacaagaagc tagcatttga accagaaaga
 781 ggtgtttttc ccaatggaaa tggcacttac ctctcctggg cagaggtgga agtctcccca
 841 caggacatag accccttctt ctgcctcata gatcacaggg ggtttttccca atctctctcg
 901 gtgcagtggg ataggacaag aaaagtaaag gatgaaaaca atgttgtagc tcagcctcag
 961 taagttaccc tctctgcctg acatgagaga ggtgaacttc agaagtcaat gtcatcaaca
1021 aggtcttcca tgggccactg tacaacagcc agcaagaatc caaggaagag gcatgggcac
1081 agaagacttg aatgccacag actgagttca ctctcaatgt cagatcaatc gccttgcctt
1141 gtaaacctcc tccttgatta atctgtcaac cctcacaatt gccctcatgc ctagaacagc
1201 acagaaagga aggcatttta aactcagaga tgctagagaa gtgtgagttg attttatcat
1261 gtattctgcc cccacatact tgattcaatt gtgaacatct tcatattcac tcaa
```

(SEQ ID NO: 22)

SEQUENCE LISTING

```
<160> NUMBER OF SEQ ID NOS: 22

<210> SEQ ID NO 1
<211> LENGTH: 72
<212> TYPE: PRT
<213> ORGANISM: Homo sapiens

<400> SEQUENCE: 1

Ala Val Asp Met Ser Gly Gly Thr Val Thr Val Leu Glu Lys Val Pro
1               5                  10                  15

Val Ser Lys Gly Gln Leu Lys Gln Tyr Phe Tyr Glu Thr Lys Cys Asn
            20                  25                  30

Pro Met Gly Tyr Thr Lys Glu Gly Cys Arg Gly Ile Asp Lys Arg His
        35                  40                  45

Trp Asn Ser Gln Cys Arg Thr Thr Gln Ser Tyr Val Arg Ala Leu Thr
    50                  55                  60

Met Asp Ser Lys Lys Arg Ile Gly
65                  70

<210> SEQ ID NO 2
<211> LENGTH: 70
<212> TYPE: PRT
<213> ORGANISM: Homo sapiens

<400> SEQUENCE: 2

Ser Ile Thr Leu Ser Cys Ser Val Ala Gly Asp Pro Val Pro Asn Met
1               5                  10                  15

Tyr Trp Asp Val Gly Asn Leu Val Ser Lys His Met Asn Glu Thr Ser
            20                  25                  30

His Thr Gln Gly Ser Leu Arg Ile Thr Asn Ile Ser Ser Asp Asp Ser
        35                  40                  45

Gly Lys Gln Ile Ser Cys Val Ala Glu Asn Leu Val Gly Glu Asp Gln
    50                  55                  60

Asp Ser Val Asn Leu Thr
65                  70

<210> SEQ ID NO 3
<211> LENGTH: 71
<212> TYPE: PRT
<213> ORGANISM: Mus sp.

<400> SEQUENCE: 3

Lys Ser Val Thr Leu Ser Cys Ser Val Gly Gly Asp Pro Leu Pro Thr
1               5                  10                  15

Leu Tyr Trp Asp Val Gly Asn Leu Val Ser Lys His Met Asn Glu Thr
            20                  25                  30

Ser His Thr Gln Gly Ser Leu Arg Ile Thr Asn Ile Ser Ser Asp Asp
        35                  40                  45

Ser Gly Lys Gln Ile Ser Cys Val Ala Glu Asn Leu Val Gly Glu Asp
    50                  55                  60

Gln Asp Ser Val Asn Leu Thr
65                  70
```

-continued

```
<210> SEQ ID NO 4
<211> LENGTH: 70
<212> TYPE: PRT
<213> ORGANISM: Rattus sp.

<400> SEQUENCE: 4

Ser Val Thr Ile Ser Cys Ser Val Gly Gly Asp Pro Leu Pro Thr Leu
1               5                   10                  15

Tyr Trp Asp Val Gly Asn Leu Val Ser Lys His Met Asn Glu Thr Ser
            20                  25                  30

His Thr Gln Gly Ser Leu Arg Ile Thr Asn Ile Ser Ser Asp Asp Ser
        35                  40                  45

Gly Lys Gln Ile Ser Cys Val Ala Glu Asn Leu Val Gly Glu Asp Gln
    50                  55                  60

Asp Ser Val Asn Leu Thr
65                  70

<210> SEQ ID NO 5
<211> LENGTH: 219
<212> TYPE: DNA
<213> ORGANISM: Homo sapiens

<400> SEQUENCE: 5
tgcagtggac atgtcgggcg ggacggtcac agtccttgaa aaggtccctg tatcaaaagg      60
ccaactgaag caatacttct acgagaccaa gtgcaatccc atgggttaca caaaagaagg     120
ctgcaggggc atagacaaaa ggcattggaa ctcccagtgc cgaactaccc agtcgtacgt     180
gcgggccctt accatggata gcaaaaagag aattggctg                            219

<210> SEQ ID NO 6
<211> LENGTH: 216
<212> TYPE: DNA
<213> ORGANISM: Mus sp.

<400> SEQUENCE: 6
tgcagtggac atgtctggcg ggacggtcac agtcctagag aaagtcccgg tatccaaagg      60
ccaactgaag cagtatttct acgagaccaa gtgtaatccc atgggttaca ccaaggaagg     120
ctgcaggggc atagacaaaa ggcactggaa ctcgcaatgc cgaactaccc aatcgtatgt     180
tcgggccctt actatggata gcaaaaagag aattgg                               216

<210> SEQ ID NO 7
<211> LENGTH: 219
<212> TYPE: DNA
<213> ORGANISM: Rattus sp.

<400> SEQUENCE: 7
tgcagtggac atgtccggtg ggacggtcac agtcctggag aaagtcccgg tatcaaaagg      60
ccaactgaag caatatttct acgagaccaa gtgtaatccc atgggttaca cgaaggaagg     120
ctgcaggggc atagacaaaa ggcactggaa ctcgcaatgc cgaactaccc aatcgtatgt     180
tcgggccctt actatggata gcaaaaagag aattggctg                            219

<210> SEQ ID NO 8
<211> LENGTH: 210
<212> TYPE: DNA
<213> ORGANISM: Homo sapiens

<400> SEQUENCE: 8
gtctatcaca ttatcctgta gtgtggcagg tgatccggtt cctaatatgt attgggatgt      60
```

-continued

```
tggtaacctg gtttccaaac atatgaatga aacaagccac acacagggct ccttaaggat    120
aactaacatt tcatccgatg acagtgggaa gcagatctct tgtgtggcgg aaaatcttgt    180
aggagaagat caagattctg tcaacctcac                                     210
```

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9

```
gagctgagcg tgtgtgacag                                                 20
```

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10

```
cttatgaatc gccagccaat                                                 20
```

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11

```
caattgtggt ttgccatctg                                                 20
```

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12

```
tgcaaaatgc acagtgaggt                                                 20
```

<210> SEQ ID NO 13
<211> LENGTH: 158
<212> TYPE: PRT
<213> ORGANISM: Homo sapiens

<400> SEQUENCE: 13

```
Met Leu Cys Leu Leu Leu Thr Leu Gly Val Ala Leu Val Cys Gly Val
1               5                   10                  15

Pro Ala Met Asp Ile Pro Gln Thr Lys Gln Asp Leu Glu Leu Pro Lys
            20                  25                  30

Ala Pro Leu Arg Val His Ile Thr Ser Leu Leu Pro Thr Pro Glu Asp
        35                  40                  45

Asn Leu Glu Ile Val Leu His Arg Trp Glu Asn Asn Ser Cys Val Glu
    50                  55                  60

Lys Lys Val Leu Gly Glu Lys Thr Glu Asn Pro Lys Lys Phe Lys Ile
65                  70                  75                  80

Asn Tyr Thr Val Ala Asn Glu Ala Thr Leu Leu Asp Thr Asp Tyr Asp
```

-continued

```
                 85               90               95
Asn Phe Leu Phe Leu Cys Leu Gln Asp Thr Thr Thr Pro Ile Gln Ser
            100             105             110

Met Met Cys Gln Tyr Leu Ala Arg Val Leu Val Glu Asp Asp Glu Ile
        115             120             125

Met Gln Gly Phe Ile Arg Ala Phe Arg Pro Leu Pro Arg His Leu Trp
    130             135             140

Tyr Leu Leu Asp Leu Lys Gln Met Glu Glu Pro Cys Arg Phe
145             150             155
```

<210> SEQ ID NO 14
<211> LENGTH: 180
<212> TYPE: PRT
<213> ORGANISM: Homo sapiens

<400> SEQUENCE: 14

```
Met Leu Cys Leu Leu Leu Thr Leu Gly Val Ala Leu Val Cys Gly Val
1               5               10              15

Pro Ala Met Asp Ile Pro Gln Thr Lys Gln Asp Leu Glu Leu Pro Lys
            20              25              30

Leu Ala Gly Thr Trp His Ser Met Ala Met Ala Thr Asn Asn Ile Ser
        35              40              45

Leu Met Ala Thr Leu Lys Ala Pro Leu Arg Val His Ile Thr Ser Leu
    50              55              60

Leu Pro Thr Pro Glu Asp Asn Leu Glu Ile Val Leu His Arg Trp Glu
65              70              75              80

Asn Asn Ser Cys Val Glu Lys Lys Val Leu Gly Glu Lys Thr Glu Asn
            85              90              95

Pro Lys Lys Phe Lys Ile Asn Tyr Thr Val Ala Asn Glu Ala Thr Leu
            100             105             110

Leu Asp Thr Asp Tyr Asp Asn Phe Leu Phe Leu Cys Leu Gln Asp Thr
        115             120             125

Thr Thr Pro Ile Gln Ser Met Met Cys Gln Tyr Leu Ala Arg Val Leu
    130             135             140

Val Glu Asp Asp Glu Ile Met Gln Gly Phe Ile Arg Ala Phe Arg Pro
145             150             155             160

Leu Pro Arg His Leu Trp Tyr Leu Leu Asp Leu Lys Gln Met Glu Glu
            165             170             175

Pro Cys Arg Phe
        180
```

<210> SEQ ID NO 15
<211> LENGTH: 180
<212> TYPE: PRT
<213> ORGANISM: Homo sapiens

<400> SEQUENCE: 15

```
Met Leu Cys Leu Leu Leu Thr Leu Gly Val Ala Leu Val Cys Gly Val
1               5               10              15

Pro Ala Met Asp Ile Pro Gln Thr Lys Gln Asp Leu Glu Leu Pro Lys
            20              25              30

Leu Ala Gly Thr Trp His Ser Met Ala Met Ala Thr Asn Asn Ile Ser
        35              40              45

Leu Met Ala Thr Leu Lys Ala Pro Leu Arg Val His Ile Thr Ser Leu
    50              55              60

Leu Pro Thr Pro Glu Asp Asn Leu Glu Ile Val Leu His Arg Trp Glu
```

-continued

| 65 | | | 70 | | | 75 | | | 80 |
|----|----|----|----|----|----|----|----|----|----|

Asn Asn Ser Cys Val Glu Lys Lys Val Leu Gly Glu Lys Thr Glu Asn
                85                        90                        95

Pro Lys Lys Phe Lys Ile Asn Tyr Thr Val Ala Asn Glu Ala Thr Leu
            100                    105                    110

Leu Asp Thr Asp Tyr Asp Asn Phe Leu Phe Leu Cys Leu Gln Asp Thr
        115                    120                    125

Thr Thr Pro Ile Gln Ser Met Met Cys Gln Tyr Leu Ala Arg Val Leu
    130                    135                    140

Val Glu Asp Asp Glu Ile Met Gln Gly Phe Ile Arg Ala Phe Arg Pro
145                    150                    155                    160

Leu Pro Arg His Leu Trp Tyr Leu Leu Asp Leu Lys Gln Met Glu Glu
                165                    170                    175

Pro Cys Arg Phe
            180

<210> SEQ ID NO 16
<211> LENGTH: 830
<212> TYPE: DNA
<213> ORGANISM: Homo sapiens

<400> SEQUENCE: 16
agcatccctc tggctccaga gctcagagcc acccacagcc gcagccatgc tgtgcctcct      60
gctcaccctg ggcgtggccc tggtctgtgg tgtcccggcc atggacatcc cccagaccaa     120
gcaggacctg gagctcccaa agttggcagg gacctggcac tccatggcca tggcgaccaa     180
caacatctcc ctcatggcga cactgaaggc ccctctgagg gtccacatca cctcactgtt     240
gcccaccccc gaggacaacc tggagatcgt tctgcacaga tgggagaaca acagctgtgt     300
tgagaagaag gtccttggag agaagactga gaatccaaag aagttcaaga tcaactatac     360
ggtggcgaac gaggccacgc tgctcgatac tgactacgac aatttcctgt ttctctgcct     420
acaggacacc accaccccca tccagagcat gatgtgccag tacctggcca gagtcctggt     480
ggaggacgat gagatcatgc agggattcat cagggctttc aggcccctgc ccaggcacct     540
atggtacttg ctggacttga aacagatgga agagccgtgc cgtttctagc tcacctccgc     600
ctccaggaag accagactcc cacccttcca cacctccaga gcagtgggac ttcctcctgc     660
cctttcaaag aataaccaca gctcagaaga cgatgacgtg gtcatctgtg tcgccatccc     720
cttcctgctg cacacctgca ccacggccat ggggaggctg ctccctgggg gcagagtctc     780
tggcagaggt tattaataaa cccttggagc atgaaaaaaa aaaaaaaaaa     830

<210> SEQ ID NO 17
<211> LENGTH: 830
<212> TYPE: DNA
<213> ORGANISM: Homo sapiens

<400> SEQUENCE: 17
agcatccctc tggctccaga gctcagagcc acccacagcc gcagccatgc tgtgcctcct      60
gctcaccctg ggcgtggccc tggtctgtgg tgtcccggcc atggacatcc cccagaccaa     120
gcaggacctg gagctcccaa agttggcagg gacctggcac tccatggcca tggcgaccaa     180
caacatctcc ctcatggcga cactgaaggc ccctctgagg gtccacatca cctcactgtt     240
gcccaccccc gaggacaacc tggagatcgt tctgcacaga tgggagaaca acagctgtgt     300
tgagaagaag gtccttggag agaagactga gaatccaaag aagttcaaga tcaactatac     360

```
ggtggcgaac gaggccacgc tgctcgatac tgactacgac aatttcctgt ttctctgcct       420
acaggacacc accaccccca tccagagcat gatgtgccag tacctggcca gagtcctggt       480
ggaggacgat gagatcatgc agggattcat cagggctttc aggcccctgc ccaggcacct       540
atggtacttg ctggacttga aacagatgga agagccgtgc cgtttctagc tcacctccgc       600
ctccaggaag accagactcc cacccttcca cacctccaga gcagtgggac ttcctcctgc       660
cctttcaaag aataaccaca gctcagaaga cgatgacgtg gtcatctgtg tcgccatccc       720
cttcctgctg cacacctgca ccacggccat ggggaggctg ctccctgggg gcagagtctc       780
tggcagaggt tattaataaa cccttggagc atgaaaaaaa aaaaaaaaaa              830
```

<210> SEQ ID NO 18
<211> LENGTH: 859
<212> TYPE: DNA
<213> ORGANISM: Homo sapiens

<400> SEQUENCE: 18

```
agcatccctc tggctccaga gctcagagcc acccacagcc gcagccatgc tgtgcctcct        60
gctcaccctg ggcgtggccc tggtctgtgg tgtcccggcc atggacatcc cccagaccaa       120
gcaggacctg gagctcccaa agttggcagg gacctggcac tccatggcca tggcgaccaa       180
caacatctcc ctcatggcga cactgaaggc ccctctgagg gtccacatca cctcactgtt       240
gcccaccccc gaggacaacc tggagatcgt tctgcacaga tgggagaaca acagctgtgt       300
tgagaagaag gtccttggag agaagactga gaatccaaag aagttcaaga tcaactatac       360
ggtggcgaac gaggccacgc tgctcgatac tgactacgac aatttcctgt ttctctgcct       420
acaggacacc accaccccca tccagagcat gatgtgccag tacctggcca gagtcctggt       480
ggaggacgat gagatcatgc agggattcat cagggctttc aggcccctgc ccaggcacct       540
atggtacttg ctggacttga aacagatgga agagccgtgc cgtttctagg tgagctcctg       600
cctggtcctg cctcctggct cacctccgcc tccaggaaga ccagactccc acccttccac       660
acctccagag cagtgggact tcctcctgcc ctttcaaaga ataaccacag ctcagaagac       720
gatgacgtgg tcatctgtgt cgccatcccc ttcctgctgc acacctgcac cacggccatg       780
gggaggctgc tccctggggg cagagtctct ggcagaggtt attaataaac ccttggagca       840
tgaaaaaaaa aaaaaaaaa                                               859
```

<210> SEQ ID NO 19
<211> LENGTH: 298
<212> TYPE: PRT
<213> ORGANISM: Homo sapiens

<400> SEQUENCE: 19

```
Met Val Arg Met Val Pro Val Leu Leu Ser Leu Leu Leu Leu Leu Gly
1               5                   10                  15

Pro Ala Val Pro Gln Glu Asn Gln Asp Gly Arg Tyr Ser Leu Thr Tyr
            20                  25                  30

Ile Tyr Thr Gly Leu Ser Lys His Val Glu Asp Val Pro Ala Phe Gln
        35                  40                  45

Ala Leu Gly Ser Leu Asn Asp Leu Gln Phe Phe Arg Tyr Asn Ser Lys
    50                  55                  60

Asp Arg Lys Ser Gln Pro Met Gly Leu Trp Arg Gln Val Glu Gly Met
65                  70                  75                  80

Glu Asp Trp Lys Gln Asp Ser Gln Leu Gln Lys Ala Arg Glu Asp Ile
                85                  90                  95
```

-continued

```
Phe Met Glu Thr Leu Lys Asp Ile Val Glu Tyr Tyr Asn Asp Ser Asn
            100                 105                 110

Gly Ser His Val Leu Gln Gly Arg Phe Gly Cys Glu Ile Glu Asn Asn
            115                 120                 125

Arg Ser Ser Gly Ala Phe Trp Lys Tyr Tyr Tyr Asp Gly Lys Asp Tyr
        130                 135                 140

Ile Glu Phe Asn Lys Glu Ile Pro Ala Trp Val Pro Phe Asp Pro Ala
145                 150                 155                 160

Ala Gln Ile Thr Lys Gln Lys Trp Glu Ala Glu Pro Val Tyr Val Gln
                165                 170                 175

Arg Ala Lys Ala Tyr Leu Glu Glu Glu Cys Pro Ala Thr Leu Arg Lys
            180                 185                 190

Tyr Leu Lys Tyr Ser Lys Asn Ile Leu Asp Arg Gln Asp Pro Pro Ser
            195                 200                 205

Val Val Val Thr Ser His Gln Ala Pro Gly Glu Lys Lys Lys Leu Lys
        210                 215                 220

Cys Leu Ala Tyr Asp Phe Tyr Pro Gly Lys Ile Asp Val His Trp Thr
225                 230                 235                 240

Arg Ala Gly Glu Val Gln Glu Pro Glu Leu Arg Gly Asp Val Leu His
                245                 250                 255

Asn Gly Asn Gly Thr Tyr Gln Ser Trp Val Val Val Ala Val Pro Pro
            260                 265                 270

Gln Asp Thr Ala Pro Tyr Ser Cys His Val Gln His Ser Ser Leu Ala
        275                 280                 285

Gln Pro Leu Val Val Pro Trp Glu Ala Ser
    290                 295
```

```
<210> SEQ ID NO 20
<211> LENGTH: 1278
<212> TYPE: DNA
<213> ORGANISM: Homo sapiens

<400> SEQUENCE: 20
ccattggcct gtagattcac ctcccctggg cagggcccca ggacccagga taatatctgt      60
gcctcctgcc cagaaccctc caagcagaca caatggtaag aatggtgcct gtcctgctgt     120
ctctgctgct gcttctgggt cctgctgtcc cccaggagaa ccaagatggt cgttactctc     180
tgacctatat ctacactggg ctgtccaagc atgttgaaga cgtccccgcg tttcaggccc     240
ttggctcact caatgacctc cagttcttta gatacaacag taaagacagg aagtctcagc     300
ccatgggact ctggagacag gtggaaggaa tggaggattg gaagcaggac agccaacttc     360
agaaggccag ggaggacatc tttatggaga ccctgaaaga catcgtggag tattacaacg     420
acagtaacgg gtctcacgta ttgcagggaa ggtttggttg tgagatcgag aataacagaa     480
gcagcggagc attctggaaa tattactatg atggaaagga ctacattgaa ttcaacaaag     540
aaatcccagc ctgggtcccc ttcgacccag cagcccagat aaccaagcag aagtgggagg     600
cagaaccagt ctacgtgcag cgggccaagg cttacctgga ggaggagtgc cctgcgactc     660
tgcggaaata cctgaaatac agcaaaaata tcctggaccg gcaagatcct ccctctgtgg     720
tggtcaccag ccaccaggcc ccaggagaaa agaagaaact gaagtgcctg gcctacgact     780
tctacccagg gaaaattgat gtgcactgga ctcgggccgg cgaggtgcag agcctgagt     840 tacggggaga tgttcttcac aatggaaatg gcacttacca gtcctgggtg gtggtggcag     900 tgccccccgca ggacacagcc ccctactcct gccacgtgca gcacagcagc ctggcccagc     960
```

-continued

```
ccctcgtggt gccctgggag gccagctagg aagcaagggt tggaggcaat gtgggatctc      1020
agacccagta gctgcccttc ctgcctgatg tgggagctga accacagaaa tcacagtcaa      1080
tggatccaca aggcctgagg agcagtgtgg ggggacagac aggaggtgga tttggagacc      1140
gaagactggg atgcctgtct tgagtagact tggacccaaa aaatcatctc accttgagcc      1200
cacccccacc ccattgtcta atctgtagaa gctaataaat aatcatccct ccttgcctag      1260
cataaaaaaa aaaaaaaa                                                    1278
```

```
<210> SEQ ID NO 21
<211> LENGTH: 307
<212> TYPE: PRT
<213> ORGANISM: Mus sp.

<400> SEQUENCE: 21

Met Val Pro Val Leu Leu Ser Leu Pro Leu Leu Leu Gly Pro Ala Val
1               5                   10                  15

Phe Gln Glu Thr Gly Ser Tyr Tyr Leu Thr Phe Leu Tyr Thr Gly Leu
                20                  25                  30

Ser Arg Pro Ser Lys Gly Phe Pro Arg Phe Gln Ala Thr Ala Phe Leu
            35                  40                  45

Asn Asp Gln Ala Phe Phe His Tyr Asn Ser Asn Ser Gly Lys Ala Glu
        50                  55                  60

Pro Val Gly Pro Trp Ser Gln Val Glu Gly Met Glu Asp Trp Glu Lys
65                  70                  75                  80

Glu Ser Gln Leu Gln Arg Ala Arg Glu Glu Ile Phe Leu Val Thr Leu
                85                  90                  95

Lys Asp Ile Met Asp Tyr Tyr Lys Asp Thr Thr Gly Ser His Thr Phe
                100                 105                 110

Gln Gly Met Phe Gly Cys Glu Ile Thr Asn Asn Arg Ser Ser Gly Ala
            115                 120                 125

Val Trp Arg Tyr Ala Tyr Asp Gly Glu Asp Phe Ile Glu Phe Asn Lys
        130                 135                 140

Glu Ile Pro Ala Trp Ile Pro Leu Asp Pro Ala Ala Ala Asn Thr Lys
145                 150                 155                 160

Leu Lys Trp Glu Ala Glu Lys Val Tyr Val Gln Arg Ala Lys Ala Tyr
                165                 170                 175

Leu Glu Glu Glu Cys Pro Glu Met Leu Lys Arg Tyr Leu Asn Tyr Ser
                180                 185                 190

Arg Ser His Leu Asp Arg Ile Asp Pro Pro Thr Val Thr Ile Thr Ser
            195                 200                 205

Arg Val Ile Pro Gly Gly Asn Arg Ile Phe Lys Cys Leu Ala Tyr Gly
        210                 215                 220

Phe Tyr Pro Gln Arg Ile Ser Leu His Trp Asn Lys Ala Asn Lys Lys
225                 230                 235                 240

Leu Ala Phe Glu Pro Glu Arg Gly Val Phe Pro Asn Gly Asn Gly Thr
                245                 250                 255

Tyr Leu Ser Trp Ala Glu Val Glu Val Ser Pro Gln Asp Ile Asp Pro
                260                 265                 270

Phe Phe Cys Leu Ile Asp His Arg Gly Phe Ser Gln Ser Leu Ser Val
            275                 280                 285

Gln Trp Asp Arg Thr Arg Lys Val Lys Asp Glu Asn Asn Val Val Ala
        290                 295                 300

Gln Pro Gln
```

305

```
<210> SEQ ID NO 22
<211> LENGTH: 1314
<212> TYPE: DNA
<213> ORGANISM: Mus sp.

<400> SEQUENCE: 22
tttcctgtgt agactgttct cccgggcact accgtagcaa tggtgcctgt cctgctgtcc      60
ctgcctctcc ttctgggtcc tgcagtcttt caggagactg ggtcttatta tctgaccttt     120
ctctacaccg ggttgtccag acccagcaaa ggttttccga ggtttcaagc cactgcattt     180
ctcaatgacc aggccttctt ccactacaac agcaacagcg ggaaggcaga gcctgtggga     240
ccttggagcc aggtggaagg aatggaggac tgggagaagg aaagccagct tcagagggcc     300
agggaggaga tcttccttgt gaccctgaaa gacatcatgg actattacaa ggacactaca     360
gggtctcaca cctttcaggg aatgtttggt tgcgagatca caaataacag aagtagtgga     420
gctgtctgga ggtatgccta cgacggagag gatttcatcg aattcaacaa agaaatccca     480
gcttggatcc ccttagaccc agcagctgca aacaccaagc taaagtggga agcagaaaag     540
gtctacgtgc agcgagccaa ggcataccta gaggaggagt gtcctgaaat gctgaagagg     600
tacctgaact acagtcgatc tcacctggac cgaatagatc ctcccactgt gacaatcacc     660
agccgtgtga tcccaggagg aaacagaata ttcaaatgcc tggcctatgg cttctaccca     720
caaagaatta gtctgcactg gaacaaggcc aacaagaagc tagcatttga accagaaaga     780
ggtgtttttc ccaatggaaa tggcacttac ctctcctggg cagaggtgga agtctcccca     840
caggacatag accccttctt ctgcctcata gatcacaggg ggttttccca atctctctcg     900
gtgcagtggg ataggacaag aaaagtaaag gatgaaaaca atgttgtagc tcagcctcag     960
taagttaccc tctctgcctg acatgagaga ggtgaacttc agaagtcaat gtcatcaaca    1020
aggtcttcca tgggccactg tacaacagcc agcaagaatc caaggaagag gcatgggcac    1080
agaagacttg aatgccacag actgagttca ctctcaatgt cagatcaatc gccttgcctt    1140
gtaaacctcc tccttgatta atctgtcaac cctcacaatt gccctcatgc ctagaacagc    1200
acagaaagga aggcatttta aactcagaga tgctagagaa gtgtgagttg attttatcat    1260
gtattctgcc cccacatact tgattcaatt gtgaacatct tcatattcac tcaa          1314
```

1

METHOD FOR DIAGNOSING AND MONITORING INFLAMMATORY DISEASE PROGRESSION

PRIORITY CLAIMS AND RELATED PATENT APPLICATIONS

This application is a continuation-in-part of and claims the benefit of priority to U.S. Utility application Ser. No. 15/094,086, filed Apr. 8, 2016, which claims the benefit of priority, under 35 U.S.C. § 120, from the US designation of International Application No. PCT/CA2014/000742, filed on Oct. 10, 2014, which claims benefit of priority from U.S. Provisional Application Ser. No. 61/889,085, filed on Oct. 10, 2013, the entire content of each of which is incorporated herein by reference in its entirety for all purposes.

FIELD OF THE INVENTION

The present invention provides compositions and/or methods for diagnosis or assessment of progression of inflammatory diseases, in particular, endometriosis.

BACKGROUND OF THE INVENTION

Neurotrophins are a family of soluble, small molecular weight proteins that act in the nervous system to promote neuronal development, differentiation, growth, and maintenance. The neurotrophin signalling network is complex. Neurotrophins can be translated as pro-proteins and cleaved into their active forms, or they can induce signalling cascades in their pro-form. Generally, the two forms have opposing functions. The neurotrophin family comprises four ligands, brain-derived neurotrophic factor (BDNF), nerve growth factor (NGF), neurotrophin 3 (NTF3), and neurotrophin 4 (NTF4), and four receptors: neurotrophic tyrosine receptor kinase (NTRK) 1, NTRK2, NTRK3, and the nerve growth factor receptor (NGFR). Although all four neurotrophins bind to NGFR with similar affinities, and their pro-protein forms have been shown to bind to this receptor as well, they are more selective in binding the NTRKs. NGF binds to NTRK1, BDNF and NTF4 bind to NTRK2, and NTF3 binds to NTRK3, each with high affinity. Another lesser known neurotrophin co-receptor, sortilin (SORT1), has been shown to interact with pro-neurotrophins in the brain and to control their release in either a constituent or activity-dependent manner. SORT1 is also involved in an elaborate intracellular trafficking network directing proteins to various fates: cell surface expression, secretion, endocytosis, or transport within the cell. However, the regulation and expression of this complex signalling network in the uterus remains unexplored.

Although mainly recognized for their supportive function within the nervous system, BDNF and its high affinity receptor NTRK2 have been shown to participate in ovarian development, follicular development, oocyte survival, endometrial stem cell neurogenesis, and normal placental development. The interaction between BDNF and NTRK2 is not only capable of inducing neuronal development, differentiation, growth, and maintenance; activation of the BDNF-NTRK2 pathway has been demonstrated to induce angiogenesis, cellular proliferation, adhesion, and resistance to apoptosis. Each of these pathways is inextricably linked to reproduction, however the mechanisms regulating the uterine expression of BDNF, NTRK2, NGFR, and SORT1 remain unknown.

Thus, it would be desirable to better understand neurotrophin regulation in the mammalian uterus, and to develop methods to recognize one or more pathologies associated with a neurotrophin.

SUMMARY OF THE INVENTION

It has now been determined that elevated expression levels of BDNF combined with one or more additional biomarkers, such as full-length Ntrk2 receptor, glycodelin and optionally, zinc-alpha-2-glycoprotein (ZAG), in a biological sample from a mammal is indicative of endometriosis.

Thus, in one aspect, a method of diagnosing endometriosis in a mammal is provided comprising the steps of: determining the expression level of BDNF in a biological sample from the mammal and comparing the BDNF level to a control BDNF level; determining the expression level of full-length Ntrk2 in the biological sample and comparing the Ntrk2 level to a control Ntrk2 level; and diagnosing the mammal with endometriosis when the BDNF level and Ntrk2 level are both elevated by at least 10% as compared with the control levels.

In another aspect, a method of diagnosing endometriosis in a mammal is provided comprising the steps of: determining the expression levels of BDNF, glycodelin, and optionally ZAG, in a biological sample from the mammal and comparing the level of each to a pre-determined level associated with endometriosis; and diagnosing the mammal with endometriosis when the levels of BDNF, glycodelin and optionally ZAG are each elevated to the predetermined level associated with endometriosis.

In another aspect, a method of monitoring a mammal following treatment for endometriosis is provided comprising: determining the expression level of a biomarker selected from BDNF, or glycodelin in a biological sample from the mammal, comparing the biomarker level to a pre-treatment level, and determining that the mammal is responding to treatment if the biomarker level is reduced by at least 10% as compared to the pretreatment biomarker level.

In a further aspect of the invention, a kit is provided comprising a BDNF-specific reactant and i) a glycodelin-specific reactant and optionally a ZAG-specific reactant, or ii) a full-length Ntrk2-specific reactant, and further optionally, instructions for use to detect endometriosis in a mammal.

In a further aspect, a method of diagnosing inflammatory disease in a mammal is provided. The method comprises determining the expression level of BDNF in a biological sample from the mammal and comparing the BDNF level to a control BDNF level to determine if the BDNF level is elevated in comparison to the BDNF baseline level, wherein an elevated BDNF level is indicative of inflammatory disease in the mammal.

These and other aspects of the invention are described herein by reference to the description and figures as follows.

US 12,607,622 B2

3

Figure 3:
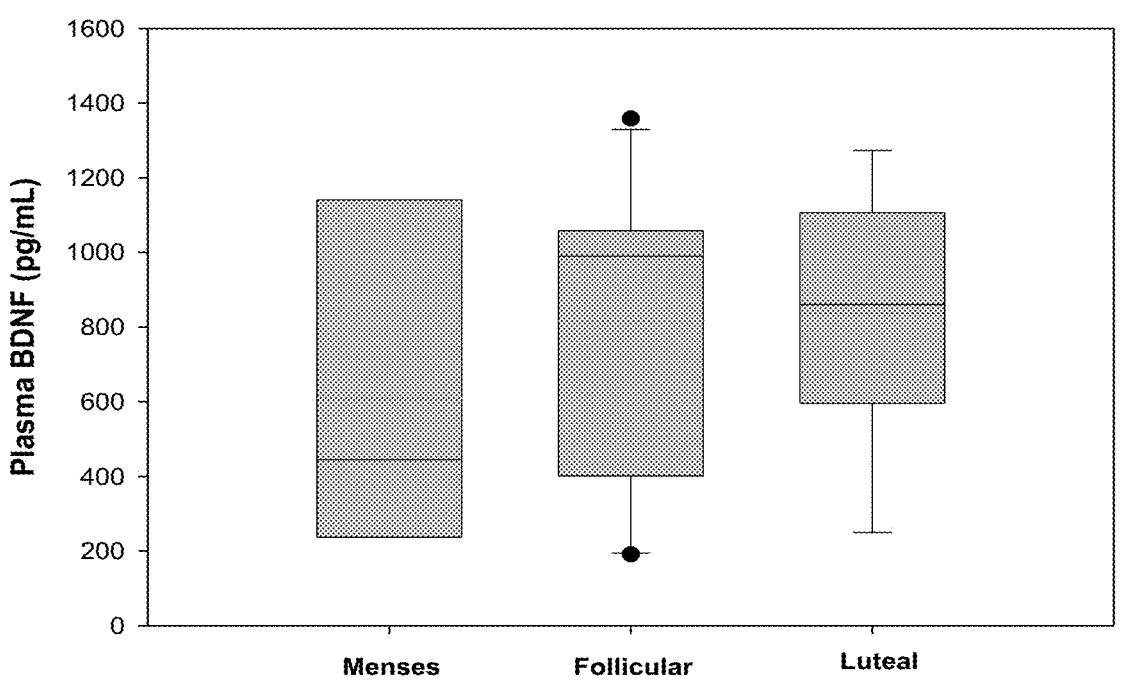
Figure 4:
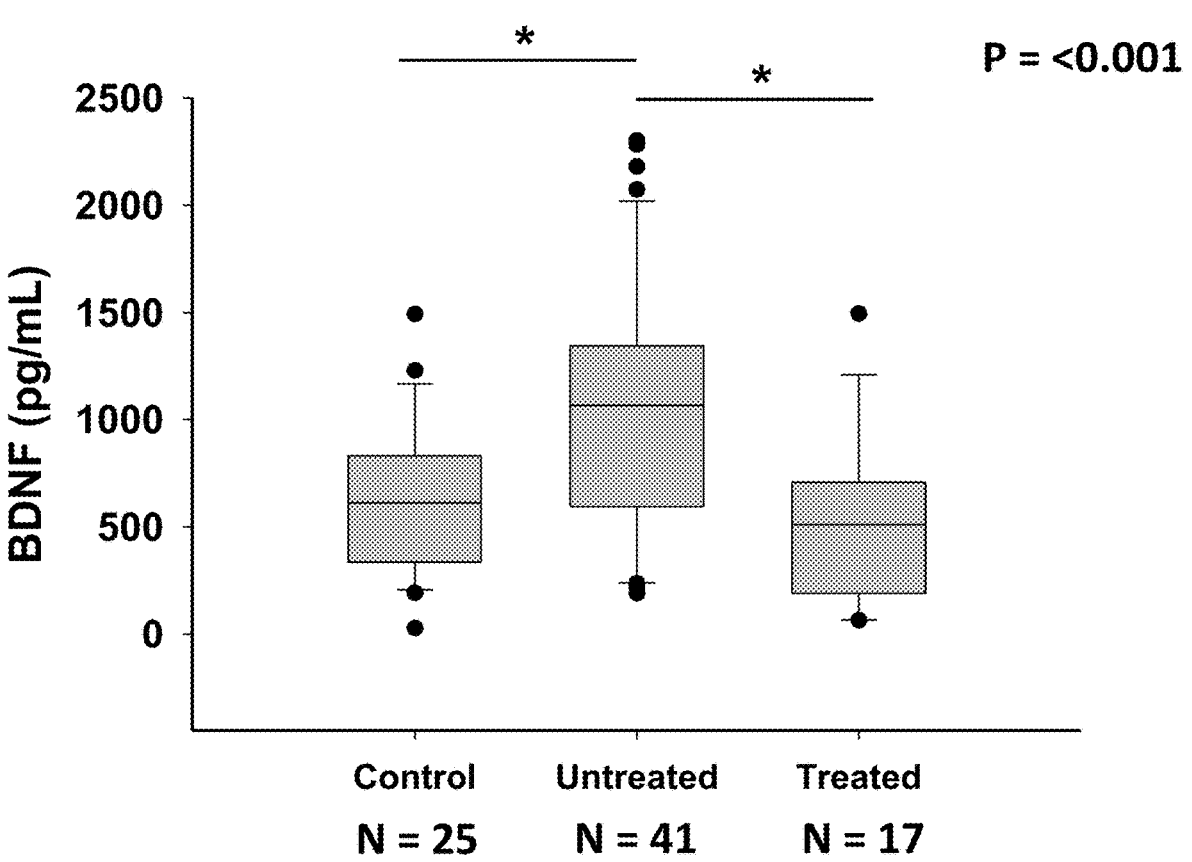
Figure 5:
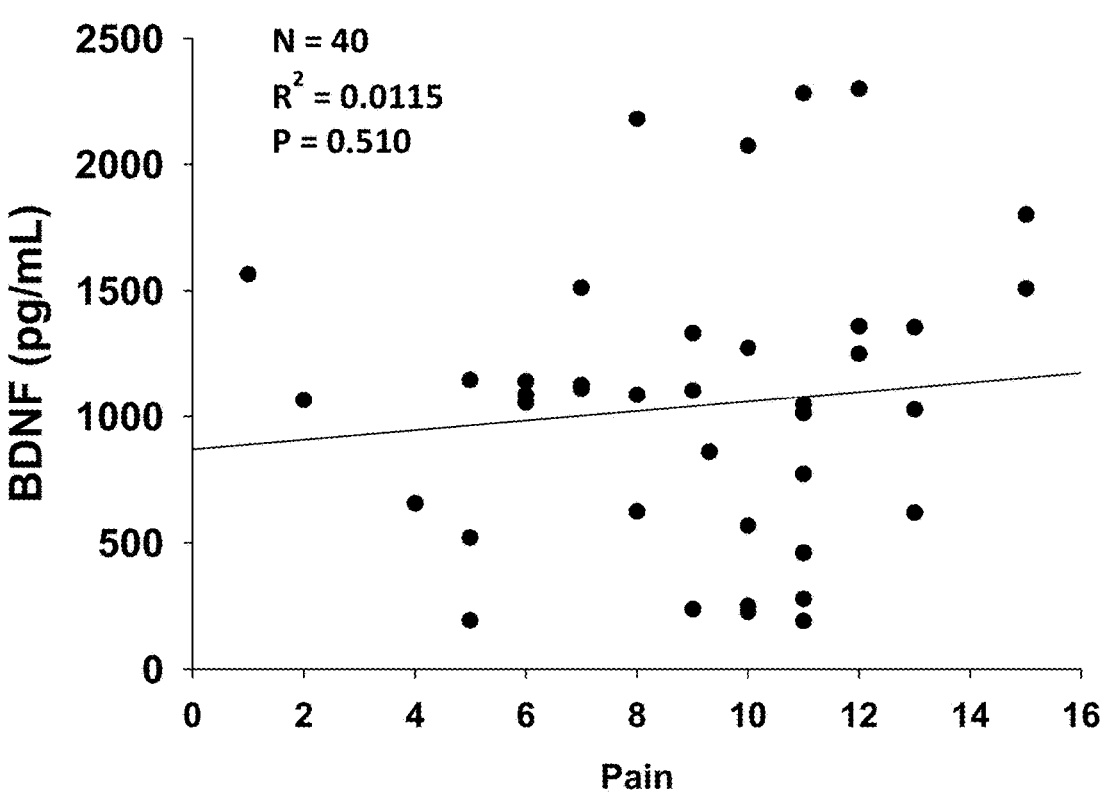
Figure 8:
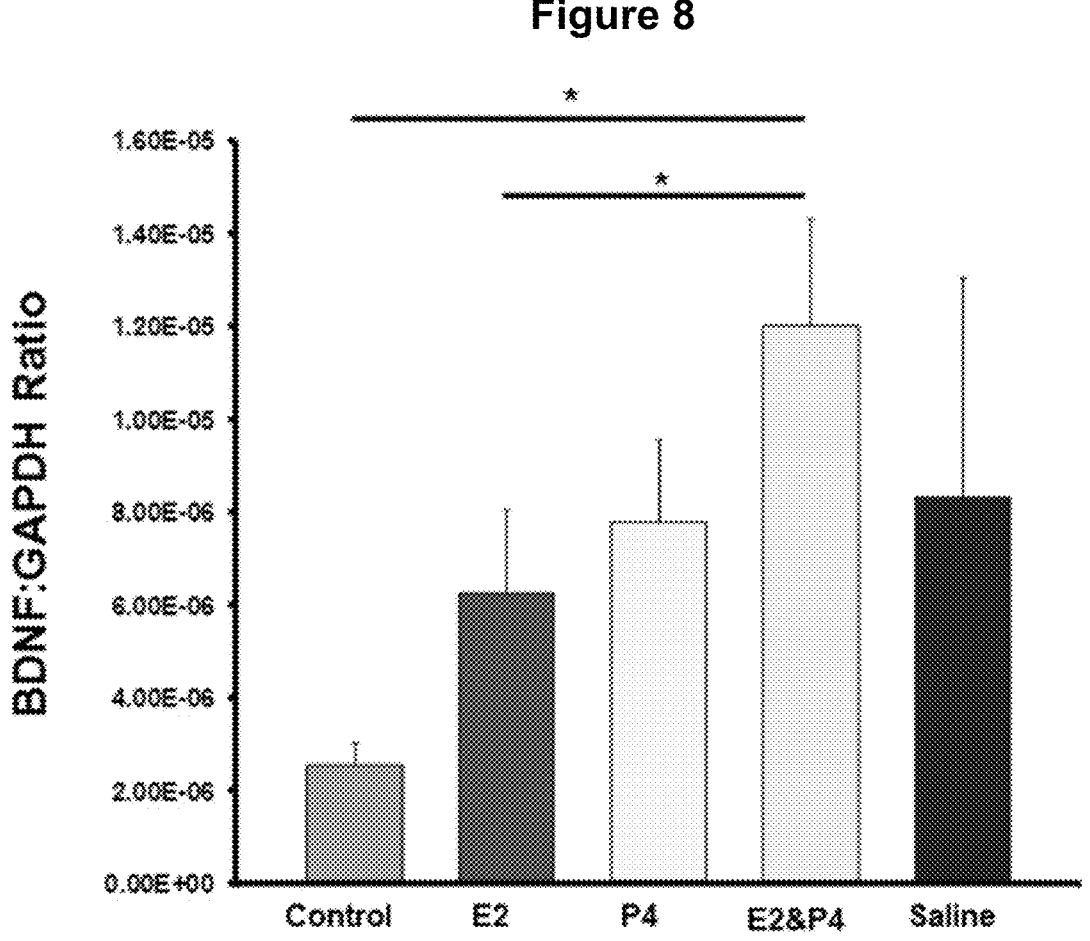
Figure 11:
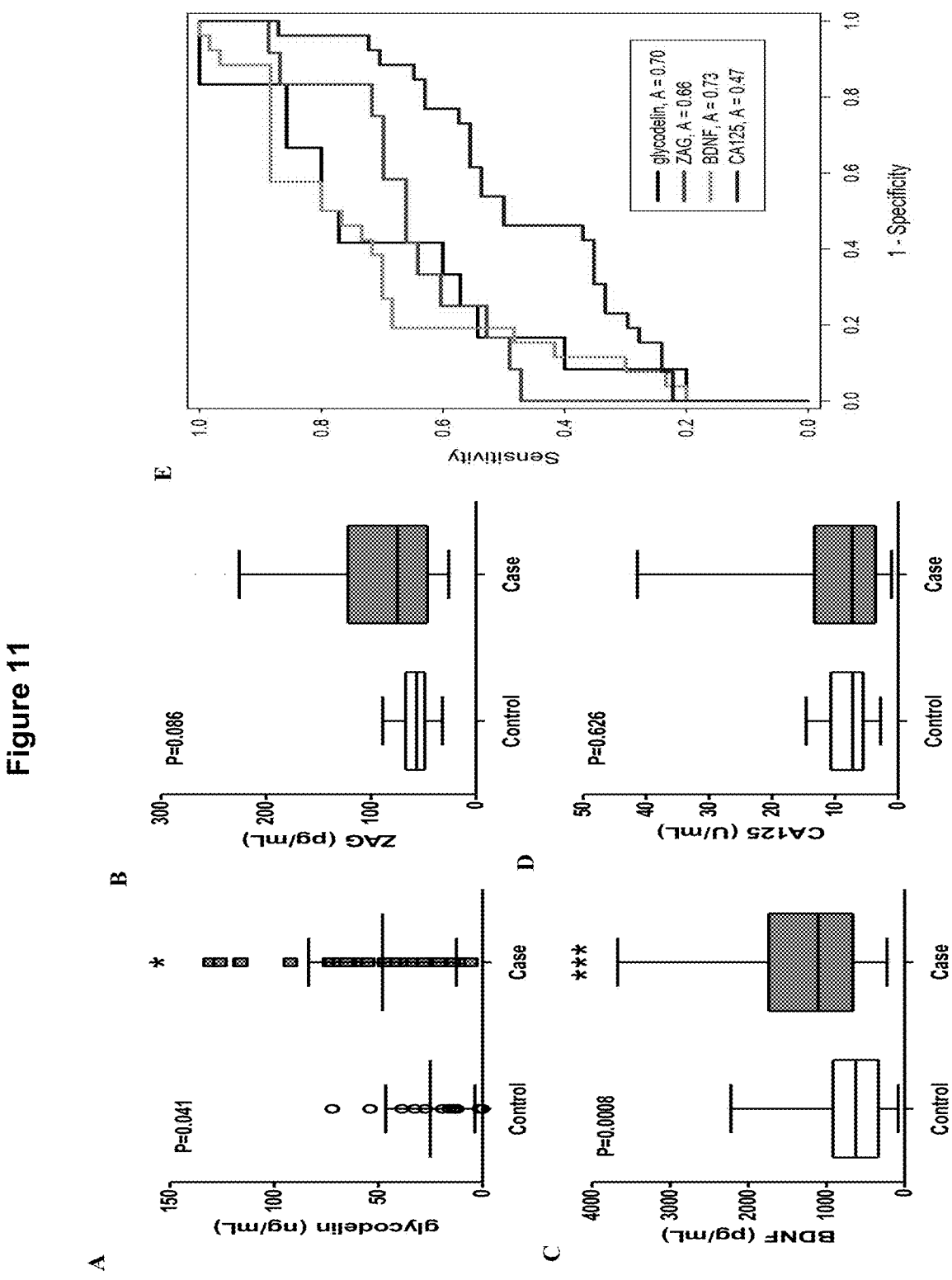
Figure 12:
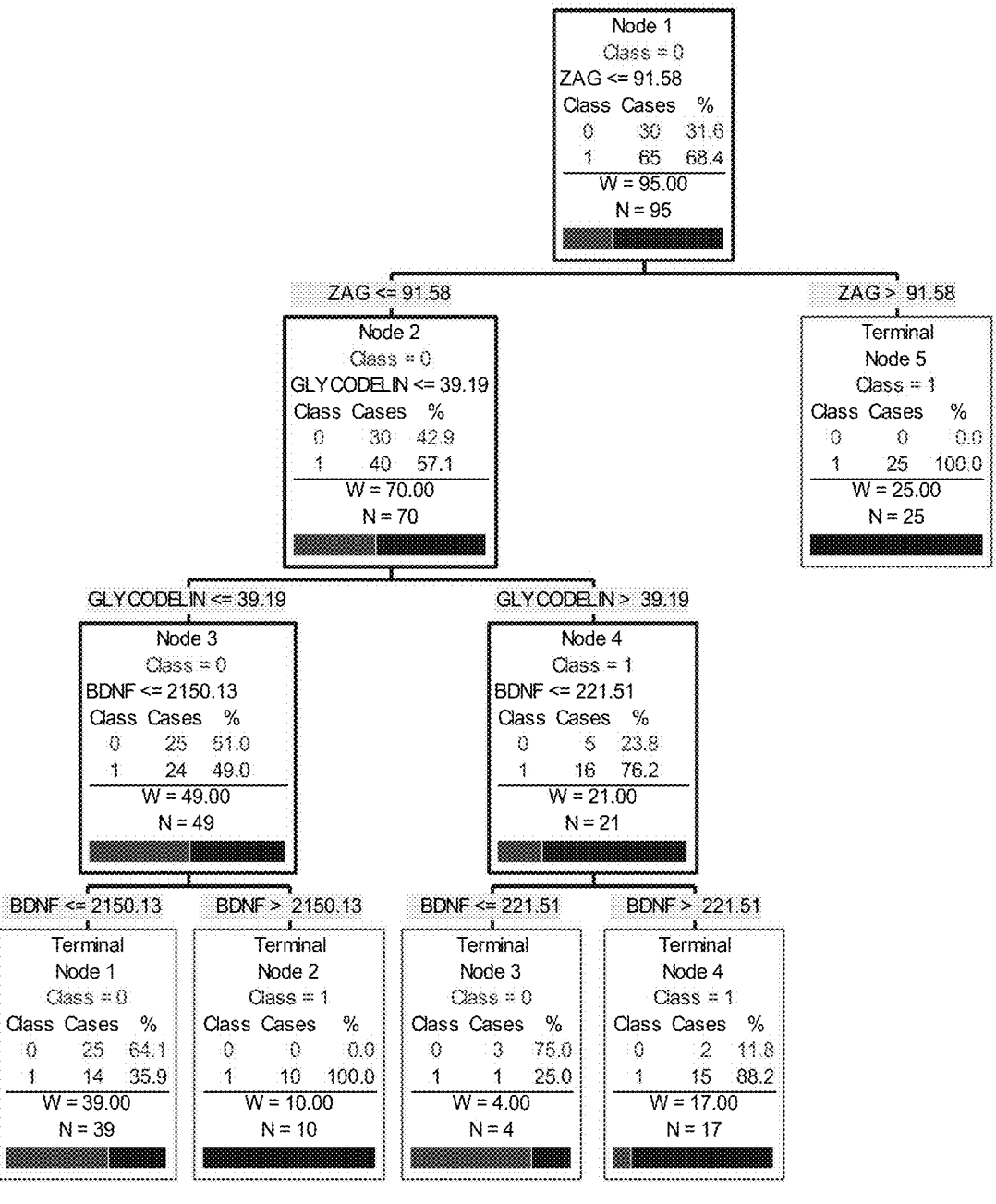
Figure 13:
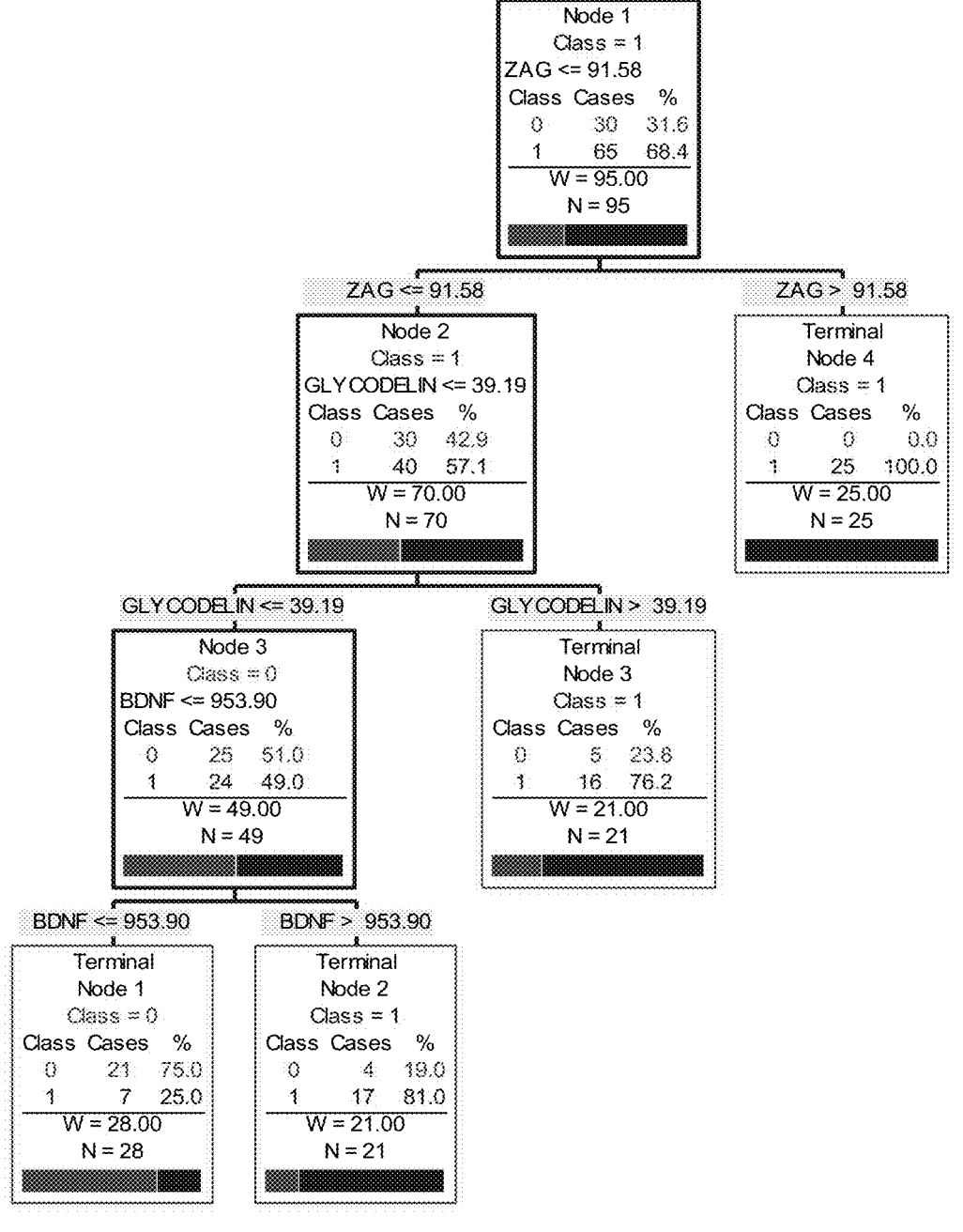

FIG. 3 graphically demonstrates that plasma total BDNF concentration is similar across the menstrual cycle;

FIG. 4 compares plasma BDNF concentration in women with endometriosis prior to treatment (untreated), and subsequent to treatment (treated);

FIG. 5 illustrates the relationship between plasma BDNF concentrations and pain scores in mammals with untreated endometriosis;

FIG. 6 shows the results of Western blot analysis of human endometrium from healthy women illustrating that pro-BDNF is the dominant form present (A), and that truncated Ntrk2 is the dominant isoform present (B);

Figure 7:
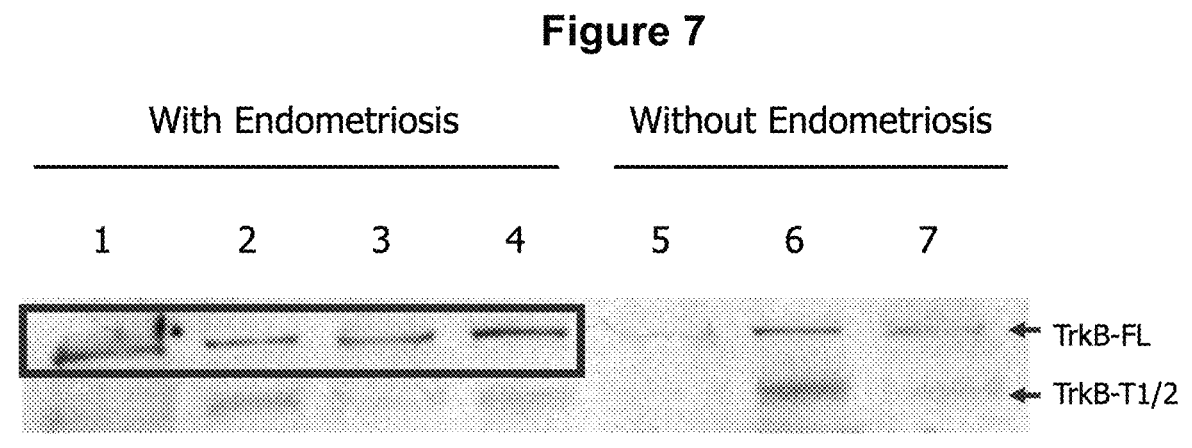

FIG. 7 shows a Western blot analysis of endometrium obtained from women with endometriosis vs. healthy controls showing that the full-length (FL) variant of Ntrk2 is overexpressed in endometriosis;

FIG. 8 illustrates BDNF transcript expression in the murine uterus in mice receiving saline (Control (n=4)), estradiol primed then estradiol (E2 (n=6)), estradiol primed then progesterone (P4 (n=6)), estradiol primed then estradiol+progesterone (E$_2$+P$_4$ (n=6)), or estradiol primed then saline (Saline (n=4));

FIG. 9 illustrates the amino acid sequences of human (A), mouse (B) and rat (C) mBDNF, and of human (D), mouse (E) and rat (F) full-length Ntrk2;

FIG. 10 illustrates the nucleic acid sequence of human (A), mouse (B) and rat (C) BDNF transcripts, and human (D), mouse (E) and rat (F) Ntrk2 transcripts;

FIG. 11 illustrates circulating concentrations of ZAG, glycodelin, BDNF, and CA-125 between untreated cases (n=35-60) and controls (n=12-26) with ROC curves. Circulating glycodelin (A) was significantly elevated (p=0.041) in untreated cases compared to controls. Circulating ZAG (B) tended to be elevated (p=0.086) in untreated cases compared to controls. Circulating BDNF (C) was significantly higher (p=0.0008) in untreated cases compared to controls while circulating concentrations of CA125 (D) did not reach statistical significance (p=0.626). Glycodelin, ZAG, BDNF, and CA-125 produced ROC curves with an AUC of 0.70 (p=0.040), 0.66 (p=0.085), 0.73 (p<0.001), and 0.47 (p=0.622), respectively. Statistically significant differences are denoted by an asterisk (*) above the graph (* p<0.05; *** p<0.001). Whiskers on the box plots represent the 5th and 95th percentiles, while the lower limit of the box lower quartile and the upper limit is the upper quartile. The line within the box is the median of the data. Normally distributed data are portrayed as an aligned dot plot with error bars representing standard deviation from the mean;

FIG. 12 illustrates that a biomarker decision tree utilizing default CART analysis parameters achieves a sensitivity of 76.9% and a specificity of 93.3%. Parent nodes are outlined by bold blue rectangles and terminal nodes are outlined by red rectangles. The class assignment of patients in each node is shown under the node number. Class 0 is the control group, and class 1 is the endometriosis group. Bars give a graphical representation of the proportion of patients from each group assigned to that node. Splitting variables are shown above a node, with the cut-off value for the split shown above the child node in gray. N=number of study participants;

FIG. 13 illustrates that a biomarker decision tree utilizing CART analysis parameters optimized for sensitivity achieves a sensitivity of 89.2% and a specificity of 70.0%. Parent nodes are outlined by bold blue rectangles and terminal nodes are outlined by red rectangles. The class assignment of patients in each node is shown under the node number. Class 0 is the control group, and class 1 is the endometriosis group. Bars give a graphical representation of the proportion of patients from each group assigned to that node. Splitting variables are shown above a node, with the cut-off value for the split shown above the child node in gray. N=number of study participants;

FIG. 14 illustrates the amino acid sequences of human isoforms of glycodelin (A, B and C), and human transcript variants of human glycodelin (D, E and F); and FIG. 15 illustrates the amino acid sequences of human (A) and mouse (B) ZAG, and mRNA sequences of human (C) and mouse (D) ZAG.

Figure 16:
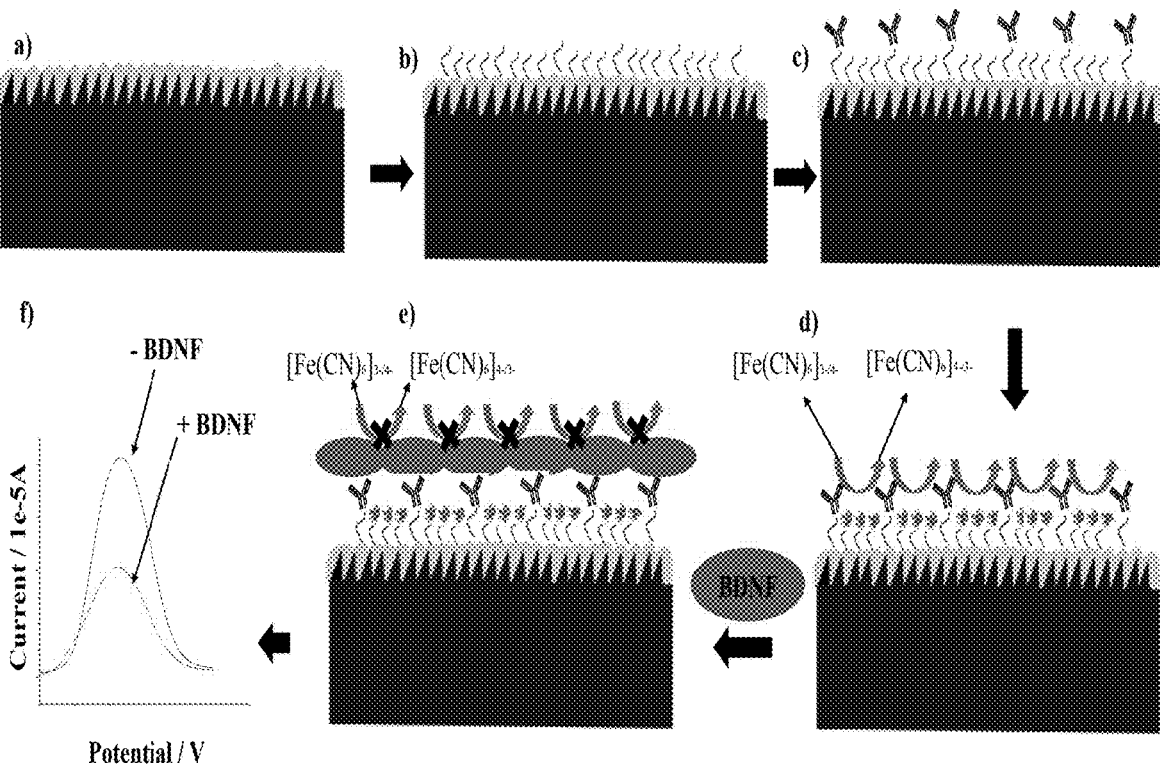

FIG. 16 is a schematic illustrating: a) APTES (3-aminopropyltiriethoxysilane) treated polystyrene (PS) substrate with porous gold immobilization surface; b) thiol bonding immobilizes the primary linker cystamine followed by an easily reactive secondary glutaraldehyde linker to create a self-assembled monolayer of aldehyde groups; c) anti-BDNF (Brain Derived Neurotrophic Factor) monoclonal antibody (mAb) is immobilized via the secondary linker to assemble the electrochemical detection device; d) unreacted aldehyde groups are blocked using 5% (w/v) Bovine Serum Albumin (BSA); e) the target analyte, BDNF protein, will attach to its mAb, and the redox reporter system of [Fe(CN)$_6$]$^{3-/4-}$ is used to electrochemically detect the presence of protein; and f) Differential Pulse Voltammetry graph illustrating how the binding of BDNF to the antibody inhibits the interfacial electron transfer reaction to take place therefore decreasing current signal.

Figure 17:
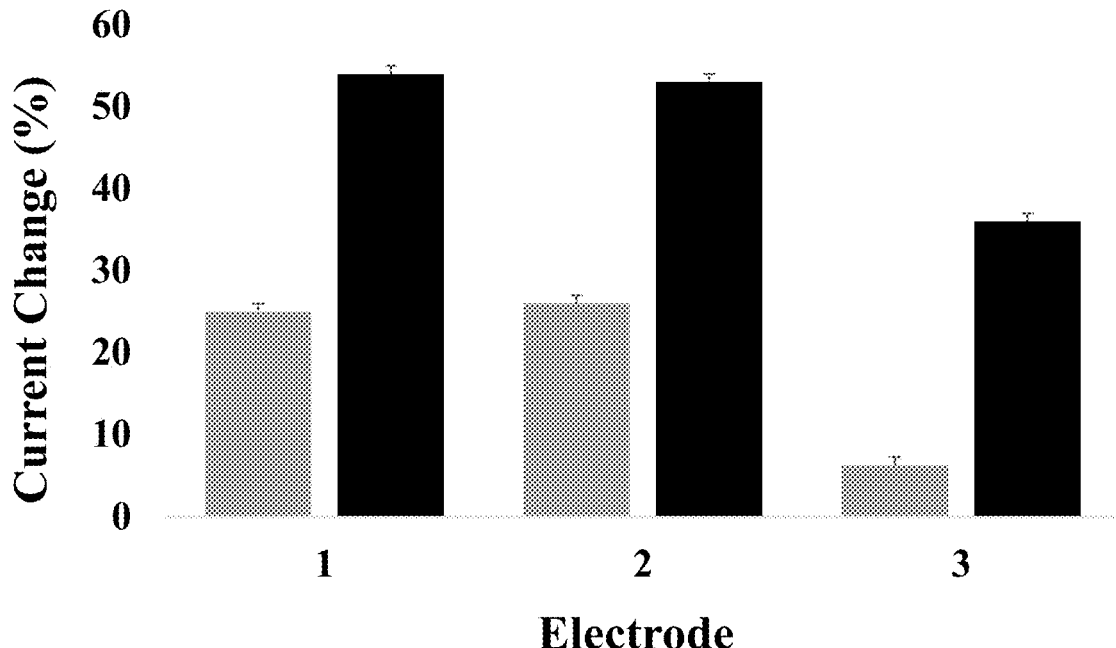

FIG. 17 graphically compares the sensitivities of planar (grey bar) and porous (black bar) immunosensors when a concentration of 1 ng/mL BDNF in PBS is used.

Figure 18:
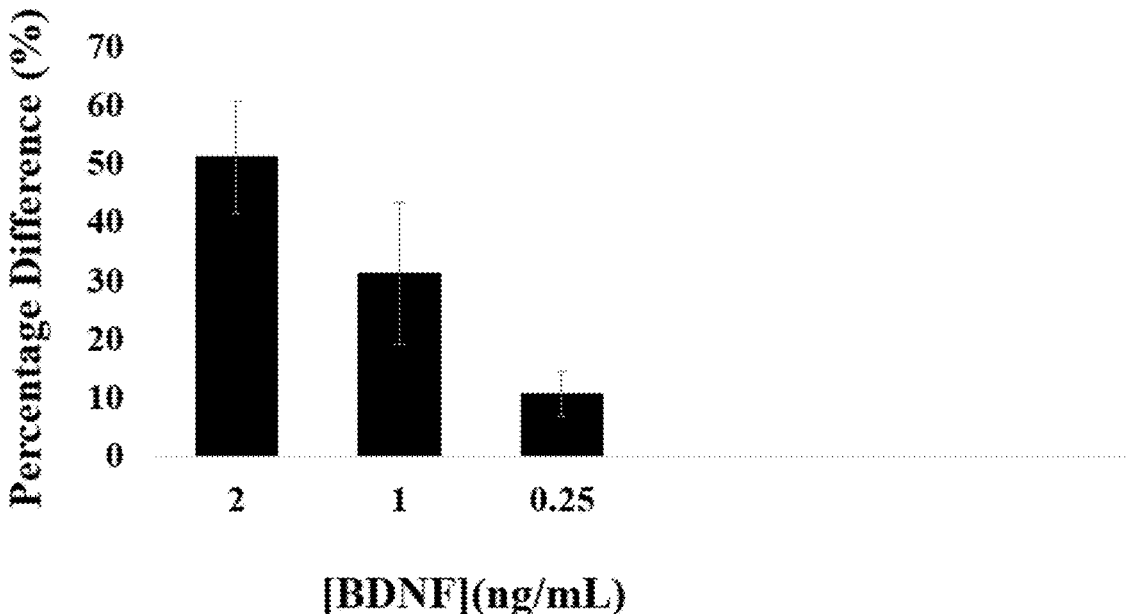

FIG. 18 graphically illustrates the detection limit of sensors in a electrochemical solution of 2.5 mM [Fe(CN)$_6$]$^{3-/4-}$ with various concentrations of BDNF in PBS.

Figure 19:
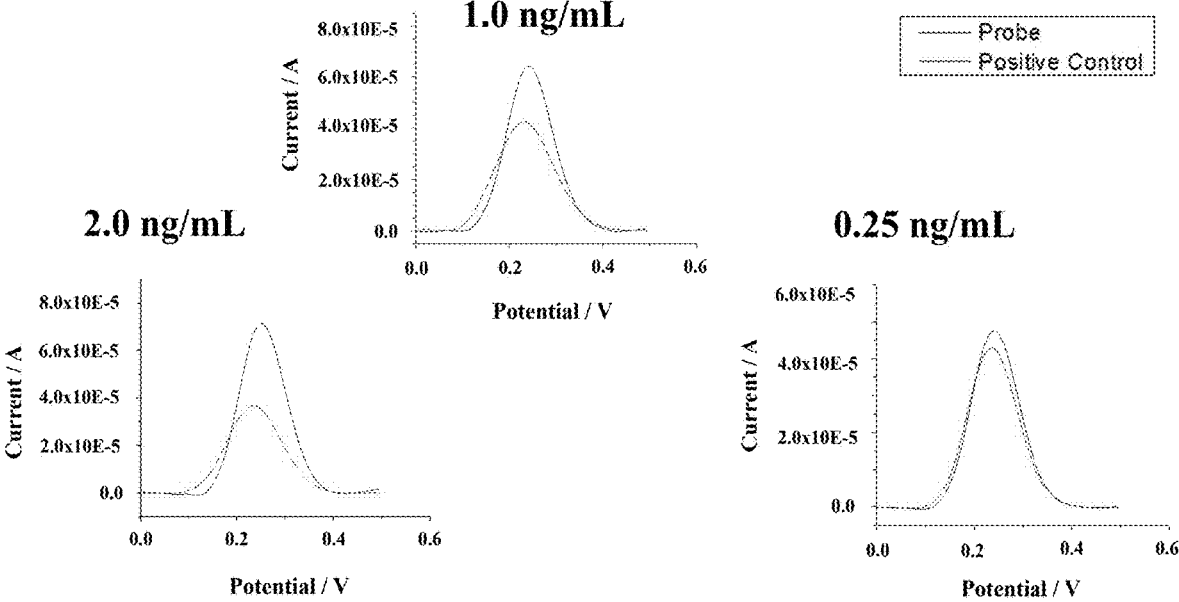

FIG. 19 illustrates differential pulse voltammograms that show the difference in electrochemical signal before and after the addition of target analyte at various concentrations.

DETAILED DESCRIPTION OF THE INVENTION

In one aspect, a method of diagnosing endometriosis in a mammal is provided comprising the steps of: determining the expression level of BDNF in a biological sample from the mammal and comparing the level to a control BDNF baseline level; determining the expression level of full-length Ntrk2 in the biological sample from the mammal and comparing the Ntrk2 level to a control Ntrk2 baseline level; diagnosing the mammal with endometriosis when the BDNF level and Ntrk2 level are both elevated by at least 10% as compared with their baseline levels.

In another aspect, a method of diagnosing endometriosis in a mammal is provided comprising the steps of: determining the expression levels of BDNF, glycodelin, and optionally ZAG, in a biological sample from the mammal and comparing the level of each to a pre-determined level associated with endometriosis; and diagnosing the mammal with endometriosis when the levels of BDNF, glycodelin and optionally ZAG are each elevated to the predetermined level associated with endometriosis.

Brain-derived neurotrophic factor, referred to herein as BDNF, is a secreted protein that supports growth and survival of neurons. As used herein, BDNF encompasses mammalian BDNF, including human and functionally equivalent variants thereof such as non-human BDNF, and isoforms or other variants of human and non-human BDNF, including pro-BDNF and mBDNF. Functionally equivalent BDNF variants are variants that incorporate alterations, such as, but not limited to, amino acid deletions, additions or substitutions, which do not significantly adversely affect BDNF activity. Post-translationally modified BNDF is referred to as mature BDNF or mBDNF. Amino acid sequences for mBDNF are known and readily accessible at sequence databases, such as GenBank, by reference to nucleotide accession nos., e.g. human mBDNF (accession no. KC855559), mouse mBDNF (accession no. KC855560), rat mBDNF (accession no. KC855561), pig mBDNF (accession no. KC855563) and horse mBDNF (accession no. KC855562). mBDNF amino acid sequences are illustrated in FIG. 9, and nucleic acid encoding sequences are shown in FIG. 10.

Neurotrophic tyrosine kinase, receptor, type 2 (Ntrk2), also known as TrkB receptor, TrkB tyrosine kinase or BDNF/NT-3 growth factor receptor, is a BDNF receptor. As used herein, Ntrk2 encompasses full-length mammalian Ntrk2, including human and functionally equivalent variants thereof such as non-human Ntrk2. Functionally equivalent variants of full-length Ntrk2 encompass full-length Ntrk2 which may incorporate alterations, such as, but not limited to, minor amino acid alternations such as deletions, additions or substitutions, e.g. involving 1 or 2 amino acid residues, which do not significantly adversely affect Ntrk2 activity, such as BDNF binding. Amino acid sequences of various forms of full-length Ntrk2 are known and readily accessible at sequence databases, such as GenBank, by reference to nucleotide accession nos., e.g. human Ntrk2 (KC855566), mouse Ntrk2 (KC855567), rat Ntrk2 (KC855568) and horse Ntrk2 (KC855569). Ntkr2 amino acid sequences are illustrated in FIG. 9, and nucleic acid encoding sequences are shown in FIG. 10.

Glycodelin, also known as progestagen-associated endometrial protein (PAEP) or pregnancy-associated endometrial alpha-2 globulin, is a protein that in humans is encoded by the PAEP gene. As used herein, glycodelin encompasses mammalian glycodelin, including human and functionally equivalent variants thereof such as non-human glycodelin, and isoforms or other variants of human and non-human glycodelin, which essentially retain the function of the parent protein. Functionally equivalent glycodelin variants are variants that incorporate alterations, such as, but not limited to, amino acid deletions, additions or substitutions, which do not significantly adversely affect activity. Amino acid sequences for glycodelin are known and readily accessible on sequence databases, such as NCBI, by reference to accession nos. e.g. human glycodelin (accession no. NP_001018058 (Isoform 2 precursor); and NP_001018059 (isoform 1 precursor)), as shown in FIG. 14A, as well as nucleotide sequences, transcript variants 1 and 2, which encode isoform 1, and transcript variant 3 which encodes isoform 2 (accession nos. NM_001018049, NM_002571 and NM_001018048, respectively) as shown in FIG. 14B.

Zinc-alpha-2-glycoprotein (ZAG) is a protein that in humans is encoded by the AZGP1 gene. As used herein, ZAG encompasses full-length mammalian ZAG, including human and functionally equivalent variants thereof such as non-human ZAG. Functionally equivalent variants of full-length ZAG encompass full-length Ntrk2 which may incorporate alterations, such as, but not limited to, minor amino acid alternations such as deletions, additions or substitutions, e.g. involving 1 or 2 amino acid residues, which do not significantly adversely affect Ntrk2 activity, such as BDNF binding. Amino acid sequences of various forms of ZAG are known and readily accessible from sequence databases, such as NCBI, by reference to accession nos., e.g. human ZAG (NP_001176) and mouse ZAG (NP_038506), as well as transcript sequences for human ZAG (NM_001185) and mouse ZAG (NM_013478) as shown in FIG. 15.

To conduct the present method, a suitable biological sample(s) is obtained from a female mammal. The term "biological sample" is meant to encompass any mammalian fluid or tissue sample that may contain nucleic acid encoding a target biomarker gene, or that may contain the target biomarker protein (such as BDNF, Ntrk2, glycodelin and/or ZAG protein or nucleic acid). Suitable biological samples include, for example, blood (including menses), serum, plasma, urine, peritoneal fluid or biopsied endometrial tissue. Any of these samples may be obtained from the mammal in a manner well-established in the art. The term "mammal" is used herein to refer to both human and non-human mammals including domestic animals, e.g. cats, dogs and the like, livestock and undomesticated animals.

Once a suitable biomarker-containing biological sample is obtained, it is analyzed to determine the expression level of selected biomarkers in the sample, either at the transcript level or protein level. As one of skill in the art will appreciate, the expression level of each biomarker may be determined using one of several techniques established in the art, including methods of quantifying nucleic acid encoding the target biomarker, such as PCR-based techniques, microarrays, gene expression system, and Northern or Southern blotting techniques, or methods of quantifying protein biomarker, such as immunological or activity assay, Western blotting, or mass spectrometry. With respect to BDNF, it is the level of mBDNF that is related to endometriosis; however, total BDNF does reflect changes in mBDNF. Thus, depending on the biological sample used, either the expression level of total BDNF may be determined, or, if possible in the sample obtained, the expression level of mBDNF may be specifically determined.

In one embodiment, the expression levels of biomarkers (e.g. BDNF, Ntrk2, glycodelin or ZAG) in a biological sample from a mammal may be determined based on the levels of nucleic acid (i.e. DNA or mRNA transcript) encoding the target protein biomarker in the biological sample. Methods of determining DNA or mRNA levels are known in the art, and include, for example, PCR-based techniques (such as RT-PCR), and Northern or Southern blotting techniques which generally include the application of gel electrophoresis to isolate the target nucleic acid, followed by hybridization with specific labeled probes. Probes for use in these methods can be readily designed based on the known sequences of genes encoding the protein biomarker, as well as the known amino acid sequence of the target biomarker, and may comprise about 15-40 nucleotides, for example, 20-35 nucleotides. Probes that target mBDNF are generally suitable for use in the present method. Such probes would detect total BDNF in a sample. For Ntrk2, probes that target full-length Nkrt2 are generally suitable to detect Ntrk2. Examples of BDNF probes include GAGCT-GAGCGTGTGTGACAG (forward) (SEQ ID NO: 9) and CTTATGAATCGCCAGCCAAT (reverse) (SEQ ID NO: 10), and examples of Ntrk2 probes include CAAT-TGTGGTTTGCCATCTG (forward) (SEQ ID NO: 11) and TGCAAAATGCACAGTGAGGT (reverse) (SEQ ID NO: 12). Suitable labels for use are well-known, and include, for example, fluorescent, chemiluminescent and radioactive labels. Probes for glycodelin and ZAG may readily be determined based on their known gene sequences, including the mRNA sequences provided herein.

A preferred assay method to measure biomarker transcript abundance includes using the NanoString nCounter gene expression system. The system utilizes a pair of probes, namely, a capture probe and a reporter probe, each comprising a 35- to 50-base sequence complementary to the biomarker transcript. The capture probe additionally includes a short common sequence coupled to an immobilization tag, e.g. an affinity tag that allows the complex to be immobilized for data collection. The reporter probe additionally includes a detectable signal or label, e.g. is coupled to a color-coded tag. Following hybridization, excess probes are removed from the sample, and hybridized probe/target complexes are aligned and immobilized via the affinity or other tag in a cartridge. The samples are then analyzed, for example using a digital analyzer or other processor adapted for this purpose. Generally, the color-coded tag on each transcript is counted and tabulated for each target transcript to yield the expression level of each transcript on the sample.

In other embodiments, the expression level of protein, mBDNF, full-length Ntrk2, glycodelin or ZAG, in a sample may be measured by immunoassay using an antibody specific to the target protein. As above, the antibody is bound to the target protein and bound antibody is quantified by measuring a detectable marker which may be linked to the antibody or other component of the assay, or which may be generated during the assay. Detectable markers may include radioactive, fluorescent, phosphorescent and luminescent (e.g. chemiluminescent or bioluminescent) compounds, dyes, particles such as colloidal gold and enzyme labels.

The term "antibody" is used herein to refer to monoclonal or polyclonal antibodies, or antigen-binding fragments thereof, e.g. an antibody fragment that retains specific binding affinity for the target biomarker. Antibodies to the target biomarkers are generally commercially available. For example, BDNF antibodies to various BDNF immunogens, including internal, and N- and C-terminal, are commercially available, for example, from Sigma Alderich, Santa Cruz Biotechnology and AbCam, while Nkrt2 antibodies are commercially available from, for example, AbCam, R&D Systems and Origene Technologies. Antibodies targeting glycodelin and ZAG are similarly commercially available from AbCam, LifeSpan BioSciences, R&D Systems, Santa Cruz Biotechnology and others. As one of skill in the art will appreciate, antibodies to the target proteins may also be raised using techniques conventional in the art. For example, antibodies may be made by injecting a host animal, e.g. a mouse or rabbit, with the antigen (target protein or immunogenic fragment thereof), and then isolating antibody from a biological sample taken from the host animal.

Different types of immunoassay may be used to determine the expression level of target proteins, including indirect immunoassay in which the protein is non-specifically immobilized on a surface; sandwich immunoassay in which the protein is specifically immobilized on a surface by linkage to a capture antibody bound to the surface; competitive binding immunoassay in which a sample is first combined with a known quantity of antibody to bind the target protein in the sample, and then the sample is exposed to immobilized target protein which competes with the sample to bind any unbound antibody. To the immobilized protein/antibody is added a detectably-labeled secondary antibody that detects the amount of immobilized primary antibody, thereby revealing the inverse of the amount of target protein in the sample.

A preferred immunoassay for use to determine expression levels of target protein in a sample is an ELISA (Enzyme Linked ImmunoSorbent Assay) or Enzyme ImmunoAssay (EIA). To determine the level or concentration of the target protein using ELISA, the target to be analyzed is generally immobilized, for example, on a solid adherent support, such as a microtiter plate, polystyrene beads, nitrocellulose, cellulose acetate, glass fibers and other suitable porous polymers, which is pretreated with an appropriate ligand for the target, and then complexed with a specific reactant or ligand such as an antibody which is itself linked (either before or following formation of the complex) to an indicator, such as an enzyme. Detection may then be accomplished by incubating this enzyme-complex with a substrate for the enzyme that yields a detectable product. The indicator may be linked directly to the reactant (e.g. antibody) or may be linked via another entity, such as a secondary antibody that recognizes the first or primary antibody. Alternatively, the linker may be a protein such as streptavidin if the primary antibody is biotin-labeled. Examples of suitable enzymes for use as an indicator include, but are not limited to, horseradish peroxidase (HRP), alkaline phosphatase (AP), ß-galactosidase, acetylcholinesterase and catalase. A large selection of substrates is available for performing the ELISA with these indicator enzymes. As one of skill in the art will appreciate, the substrate will vary with the enzyme utilized. Useful substrates also depend on the level of detection required and the detection instrumentation used, e.g. spectrophotometer, fluorometer or luminometer. Substrates for HRP include 3,3',5,5'-Tetramethylbenzidine (TMB), 3,3'-Diaminobenzidine (DAB) and 2,2'-azino-bis(3-ethylbenzothiazoline-6-sulphonic acid) (ABTS). Substrates for AP include para-Nitrophenylphosphates. Substrates for ß-galactosidase include β-galactosides; the substrate for acetylcholinesterase is acetylcholine, and the substrate for catalase is hydrogen peroxide.

As will be appreciated by one of skill in the art, assay methods which target the activity of a target protein may also be utilized to determine the expression level thereof in a sample. In this regard, suitable assays would be known to the skilled person, including for example, an mBDNF-Nkrt2 binding assay.

The expression level of the selected biomarkers mBDNF and Nkrt2, or mBDNF, glycodelin and optionally ZAG, in a given sample may be analyzed individually or together using, for example, biochip array technology. Generally, biochip arrays provide a means to simultaneously determine the level of multiple biomarkers in a given sample. These arrays may utilize ELISA technology and, thus, the biochip may be modified to incorporate capture antibodies for each target at pre-defined sites on the surface.

Once the expression level of selected biomarkers in a biological sample of a mammal has been determined, these expression levels are compared to control expression levels, i.e. the expression level of selected biomarkers from BDNF, Ntrk2, glycodelin and ZAG, in a healthy control, i.e. a mammal that does not have endometriosis. Alternatively, the level of the selected biomarkers may be compared to the expression level of a "housekeeping gene". The term "housekeeping gene" as used herein is meant to refer to a gene that encodes a protein product that is not connected to, involved in or required for processes specific to endometriosis, and thus, exhibits a fixed expression level in mammals with and without endometriosis. Examples of suitable housekeeping genes include, but are not limited to, genes encoding ACTB (Beta-actin), GAPDH (Glyceraldehyde 3-phosphate dehydrogenase), RPLP0 (60S acidic ribosomal protein P0), GUSB (beta-glucuronidase), and TFRC (transferring receptor 1). In a comparison of the expression levels of target biomarkers to housekeeping genes, a determination of an increase in transcript abundance or expression of the selected biomarker relative to that of the housekeeping gene is indicative of endometriosis.

The level of expression (or concentration) that would be considered to represent an increased or elevated expression level of the selected biomarkers that is associated with endometriosis in accordance with the present method may be determined relative to levels of biomarker in a healthy control sample, or relative to the expression of one or more housekeeping genes. In one embodiment, a reproduceable statistically significant increase in the expression of a biomarker, for example, an increase of at least about 5%, preferably, at least about 10%, 20%, 30%, 40% or 50% or greater, in comparison to the expression levels in a control, or in comparison to the expression level of a housekeeping gene, is considered to be elevated expression that is relevant with respect to a diagnosis of endometriosis. Generally, a plasma BDNF level in the range of about 100-500 pg/ml is considered to be normal, while plasma BDNF levels higher than this, e.g. by about 10-50% or greater, are indicative of endometriosis, e.g. for example, plasma BDNF levels of 800 pg/ml or greater are indicative of endometriosis. Generally, serum concentrations of glycodelin in the range of 5 to 31 ng/ml is considered to be normal, and concentrations greater than 39 ng/ml are considered to be indicative of endometriosis. For ZAG, circulating concentrations in the range of 41 to 65 pg/ml are regarded as normal, while serum concentrations greater than 92 pg/ml are considered to be indicative of endometriosis. As one of skill in the art will appreciate, the difference in the level of biomarker expression as compared to expression of the housekeeping gene(s) may vary with the methodology employed to quantify and analyze nucleic acid and/or protein expression.

The present invention also provides a method of diagnosing the stage of endometriosis. Levels of BDNF exhibit a greater increase in comparison to normal controls at stage I-II of endometriosis than at stage while levels of glycodelin exhibit a greater increase in comparison to normal controls at stage III-IV of endometriosis than at stage I-II. Thus, levels of BDNF which are greater than 30%, and preferably, 40-50% greater than control levels, are indicative of stage I-II endometriosis, and levels of glycodelin which are greater than 30%, and preferably, 40-50% greater than control levels, are indicative of stage III-IV endometriosis.

Once a mammal has been diagnosed with endometriosis, the mammal can then be appropriately treated. In mild cases, the appropriate treatment may be administration of a pain medication, such as nonsteroidal anti-inflammatory drugs (NSAIDs), e.g. ibuprofen or naproxen, to address painful cramps. Alternatively, hormone therapy may be utilized to address the pain mild to moderate endometriosis, including, hormonal contraceptives (birth control pills, patches and vaginal rings); gonadotropin-releasing hormone (Gn-RH) agonists and antagonists to block the production of ovarian-stimulating hormones, lowering estrogen levels and preventing menstruation, optionally in combination with a low dose of estrogen or progestin to decrease menopausal side effects; progestin therapy, e.g. such as an intrauterine device (Mirena™), contraceptive implant or contraceptive injection (Depo-Provera™); and steroid treatment (e.g. danazol) to suppress the growth of the endometrium. For severe endometriosis, treatment by surgery is appropriate.

In another aspect, a method to monitor response by a mammal to treatment for endometriosis, including surgical or drug therapy (e.g. hormone therapy), is also provided. The method of monitoring a mammal following treatment of endometriosis comprises: determining the expression level of a selected biomarker, e.g. BDNF or glycodelin, in a sample from the mammal and comparing the level to a pre-treatment biomarker expression level to determine if the biomarker level has decreased in comparison to the pre-treatment biomarker level. A significant decrease, i.e. a decrease of at least about 10% or greater, preferably at least about 20% or greater, e.g. 30-50% or greater in the biomarker BDNF level compared to the pre-treatment level indicates that the mammal is responding to the treatment.

Disease recurrence may also be monitored in a mammal previously successfully treated for endometriosis using a method in accordance with the invention. A method as used to diagnose endometriosis in a first instance would be applicable. In particular, biomarker levels, e.g. BDNF expression levels, either total BDNF or mBDNF, and Ntrk2 expression levels, or BDNF, glycodelin and optionally ZAG levels, are determined in a relevant biological sample from the mammal as described. It is then determined whether or the biomarker levels represent a significant increase in comparison to control values, or in comparison to the level of a selected housekeeping gene, wherein a significant increase (e.g. 10-50% or greater) in the biomarker levels is indicative of disease recurrence.

In a further embodiment of the invention, a kit for use in detecting endometriosis is provided comprising reactants for the specific identification of selected biomarkers, including a BDNF-specific reactant and a full-length Ntrk2-specific reactant, or a BDNF-specific reactant, a glycodelin-specific reactant and optionally a ZAG-specific reactant. Instructions for use in methods of diagnosing and/or monitoring disease recurrence, disease progression or treatment of endometriosis in a mammal may also be provided. As set out above, biomarker-specific reactants may include nucleic acid probes or antibodies based on the known nucleic acid and amino acid sequences of the selected biomarkers. A substrate for each biomarker may also be used as a reactant. The reactants may be associated with an indicator (e.g. an enzyme, such as horseradish peroxidase (HRP), alkaline phosphatase (AP), ß-galactosidase, acetylcholinesterase and catalase) such that the interaction of the reactant with BDNF and Ntrk2 yields a product or signal, releases the enzyme that is readily detectable and indicative of BDNF and Ntrk2 in the biological sample.

The kit may be provided in the form of a biochip which incorporates at least the selected biomarker-specific reactants, such as a BDNF-specific reactant (or mBDNF reactant) and/or a full-length Ntrk2-specific reactant, or BDNF-, glycodelin- and optionally ZAG-specific reactants, or all of the above, at pre-defined sites on the surface thereof. The reactants are each associated with an indicator such that in the presence of the targeted biomarker, a detectable product or signal is released, as above. The biochip may be adapted for use with a blood sample, e.g. from a finger prick, or a menses sample.

In another embodiment, a biochip adapted for the electrochemical detection of circulating target biomarkers is provided. One or more biomarker-specific reactants, e.g. a BDNF-specific reactant, such as an antibody, and optionally, an Ntrk2-specific reactant, or BDNF-, glycodelin- and optionally ZAG-specific reactants, is/are bonded to circuits, e.g. an electrode, in a silicone microchip. When a target biomarker such as BDNF from a sample binds to its specific reactant, it alters the voltage potential measured across the probe resulting in a measurable electrical output that is detectable by transducers in the device and which is proportional to the concentration of BDNF in the sample.

Thus, in one embodiment, a device comprising a 3 electrode system is provided. The device comprises one or more working electrodes adapted to bind with target analyte (e.g. BDNF, full-length Ntrk2, glycodelin, and optionally, ZAG), i.e. the working electrode has bound thereto bio-marker-specific reactant that binds to the target analyte(s); a reference electrode with a known reduction potential (acts as reference in measuring and controlling the working electrode's potential and at no point does it pass any current); and an auxiliary or counter electrode that passes all the current needed to balance the current observed at the working electrode. In use, the electrode system, submerged in electrolyte comprising a redox reporter, produces an electrochemical signal which decreases in the presence of target analyte (which blocks access of the redox reporter to the electrode surface). The degree of signal change correlates with the concentration level of the target analyte. Thus, the device is useful to detect the levels of target biomarkers, to determine whether the biomarker levels are associated with endometriosis.

Measurement of plasma concentrations of total and/or mBDNF is potentially valuable as a method to measure non-specific inflammation in a mammal that may be useful to prompt further investigation into the cause thereof. Thus, in another aspect, a method of diagnosing inflammation-causing disease in a mammal is provided. The method comprises determining the level of BDNF in a BDNF sample from the mammal and comparing the level to a control BDNF baseline level to determine if the BDNF level is elevated in comparison to the BDNF baseline level, wherein an elevated BDNF level is indicative of inflammation-causing disease in the mammal. Inflammation-causing disease may include, for example, cancer such as ovarian cancer and other endocrine tumors, lupus, Crohn's disease, ulcerative colitis, polycystic ovarian syndrome and periodontal disease.

Embodiments of the invention are described by reference to the following specific examples which are not to be construed as limiting.

Example 1—BDNF Determination by Immunoassay

Materials and Methods

Study Participants. Women undergoing surgery for endometriosis (cases, N=76) or other benign gynaecological surgeries (symptomatic controls, N=20) were recruited prospectively. Women with no history of pelvic pain, who were not undergoing surgery were also recruited (asymptomatic controls, N=18). Study participants completed demographics and gynecological history questionnaires. Menstrual cycle length, date of last menstruation, and pelvic pain assessed on a 5 question, 5-point visual analog scale was recorded for each participant. Women who underwent laparoscopic surgery were categorized as a case or symptomatic control by a gynaecological surgeon, and the diagnoses were later confirmed with pathology reports. The stage of endometriosis was determined during surgery according to the revised Classification of the American Society of Reproductive Medicine. All study participants completed written informed consents and the study was approved by the Hamilton Health Sciences Integrated Research Ethics Board, McMaster University (IRB #06-064, and 12-083-T).

A trained research nurse collected peripheral blood from the cubital vein from each participant in plasma separator tubes (BD Canada, Mississauga, ON, Canada). Blood was placed on ice, transported to the laboratory, and processed according to established Standard Operating Procedures (SOPs: MAC-OG-RBF-001 to MAC-OG-RBF-006). Immediately after plasma separation, plasma was divided into 1.8 mL cryovials (Sigma-Aldrich Chemical Company, St. Louis. MO) and frozen at −80° C. until required for assay.

Exclusions. Individuals unable to provide consent, or under the age of 18 were excluded from the study. Women were also excluded from the study if they had a diagnosis of adenomyosis (4.4%), polycystic ovary syndrome (0.9%), or if the pathological findings did not correlate with the clinical impression (4.4%). Plasma samples were excluded from the study if they were hemolyzed (13.2%).

BDNF Assay. Plasma samples were thawed at room temperature and circulating BDNF was quantified in triplicate using the BDNF Emax immunoassay ELISA (Promega, Madison, WI, USA), following the manufacturer's protocol. Briefly, 96 well NUNC maxisorp plates were coated with anti-human BDNF antibody (provided with the kit) overnight. They were blocked the following morning using the block and sample buffer provided in the kit. Freshly thawed plasma samples were diluted 1:10 with sample buffer provided in the kit. Following the BDNF ELISA, the absorbance was read at 450 nm within 30 minutes using the Biotek Synergy spectrophotometer (Fisher Scientific, Ottawa, ON, Canada). BDNF concentration and % CV of the triplicates were calculated by the Biotek Synergy software.

Figure 1:
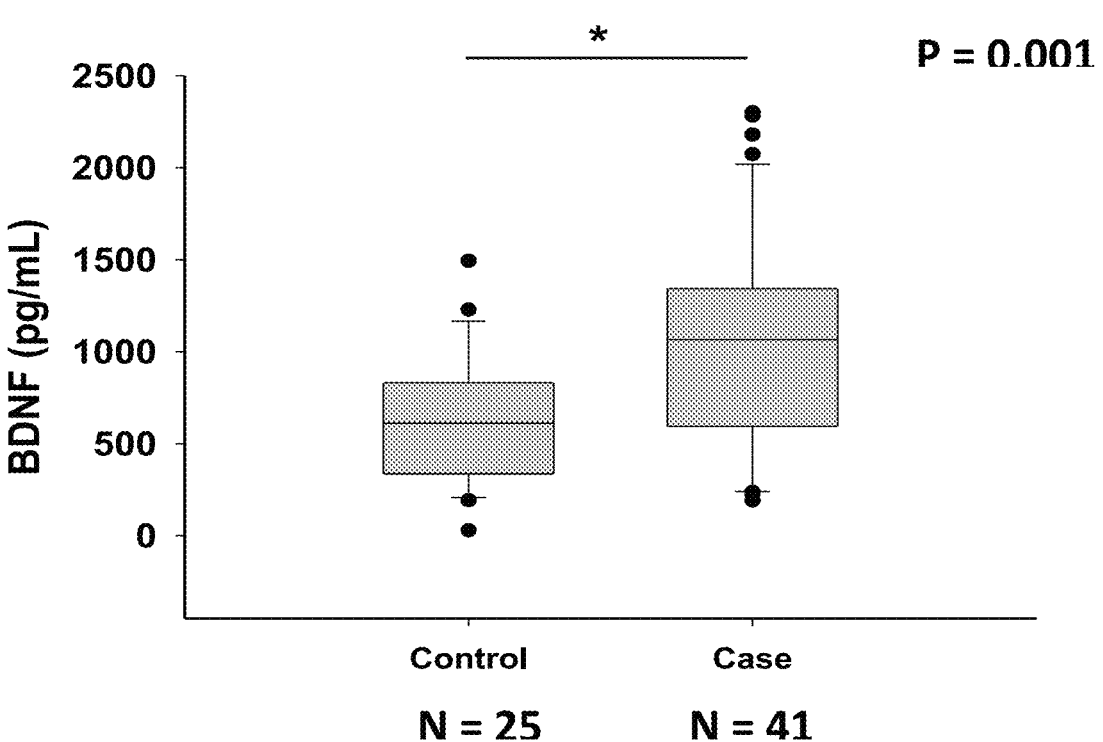
FIG. 1 graphically illustrates that circulating concentration of BDNF is higher in the plasma of women with endometriosis vs. a control population.
Figure 2:
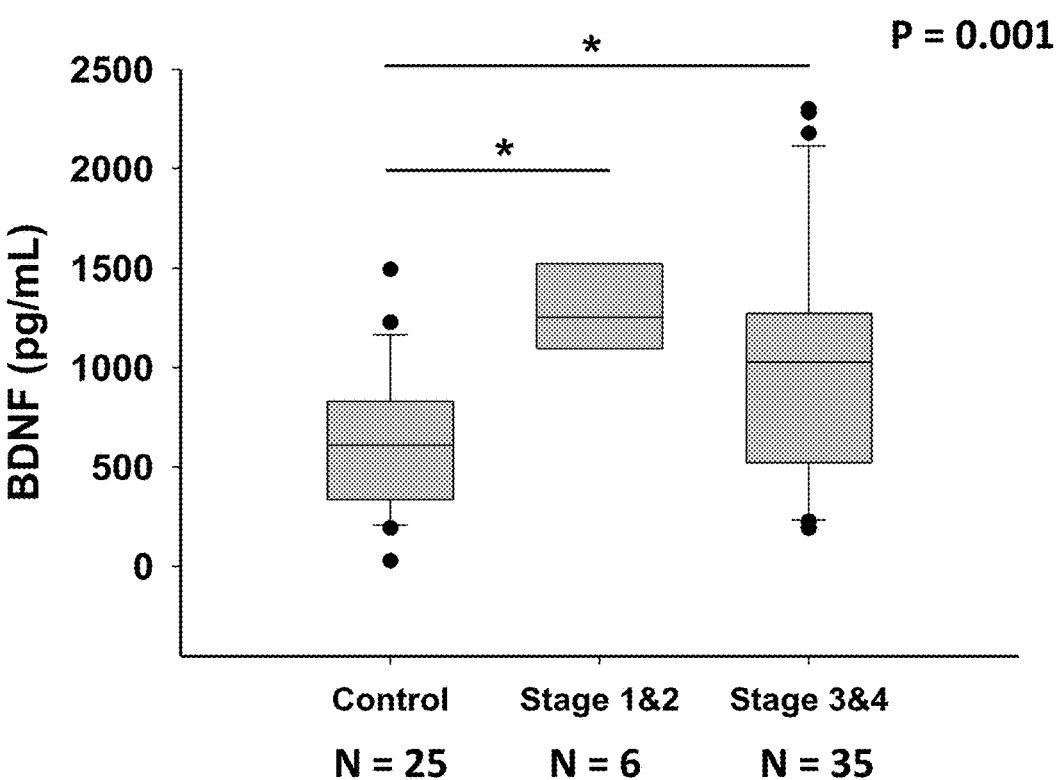
FIG. 2 graphically illustrates that total plasma BDNF concentration is significantly higher in women at any stage of endometriosis vs. controls.

Data and Statistical Analysis. The intra-sample variation (triplicates) did not exceed 15% (% CV<15) in any plasma sample. A Grubb's test (http://graphpad.com/quickcalcs/Grubbs1.cfm) was used to identify statistical outliers (2.6%) which were omitted from analysis and values found to be non-detectable by ELISA (1.8%). Data were compared by t-test, one-way ANOVA, or linear regression (SigmaStat 3.5 Systat Software Inc., Chicago, IL, USA). A P value of <0.05 was considered significant. Data are presented as box plot with lines representing the $25^{th}$, 50th, and 75th percentiles. Results:

Circulating concentrations of BDNF were found to be higher in the plasma of women with endometriosis vs. symptomatic and asymptomatic controls as shown in FIG. 1. The data included only women not receiving hormone treatment for endometriosis. The control group was composed of 36% symptomatic and 64% asymptomatic mammals. The endometriosis group included mammals in endometriosis stages I and II (15%) and stages III and IV (85%). Comparisons were made by t-test. Mean total plasma BDNF concentrations were significantly higher in women with stage I and II endometriosis, and with stages III and IV endometriosis vs. controls (see FIG. 2). Data were compared by one-way ANOVA and appropriate posthoc comparison test.

A comparison of plasma total BDNF concentrations across the menstrual cycle (menses, follicular and luteal) indicated that the concentration was similar during the entire cycle (see FIG. 3).

Plasma BDNF concentrations were compared in controls (women without endometriosis), women with endometriosis prior to ovarian suppression treatment (untreated), and women with endometriosis who were being treated for their disease with ovarian suppressing hormone treatments (oral contraceptives or Lupron). These results showed that treatment of endometriosis resulted in a decrease in plasma BDNF to levels comparable to control levels (FIG. 4). Data were compared by one-way ANOVA and appropriate post-hoc test.

A comparison of plasma BDNF concentrations against pain was also conducted. BDNF plasma concentrations were found to be positively correlated with pain scores, which is a primary presenting complaint of mammals with endometriosis. Linear Regression performed using pain as the dependent variable and plasma BDNF concentration as the independent variable.

Example 2—mBDNF and Ntrk2 Expression Linked to Endometriosis

Western blot analysis of BDNF and Ntrk2 from human endometrium of healthy women was conducted. Extracted protein (60 mg) from human endometrium was run on a 4-20% gradient gel (Thermo-Scientific) at 150 V for 50 minutes. Protein was transferred to PVDF membrane (VWR International, Mississauga, ON, Canada) at 40 V for 90 minutes. Blots were blocked for 1 hour at room temperature with 5% skim milk/TBS-T, and subsequently probed with 1:1000 rabbit anti-BDNF (Abcam) or 1:1000 rabbit anti-Ntrk2 (Abcam), overnight at 4° C. Anti-Rabbit-ECL secondary (GE, Mississauga, ON, Canada) at a concentration of 1:5000 was applied for 1 hour at room temperature, blots were briefly washed in TBS-T and TBS, then incubated with ECL substrate (Thermo-Scientific) for 5 minutes. Exposures were performed using x-ray film (Thermo-Scientific), and the exposure times were 60, and 45 minutes for BDNF and Ntrk2 respectively. Mouse brain was used as a positive control, and beta-actin as a loading control.

BDNF in the Human Uterus. pro-BDNF (35 kDa) was found to be the dominant form present whereas mBDNF was not detectable (FIG. 6A). A similar analysis was conducted on endometrium from women with endometriosis and the mBDNF form was overexpressed as compared to the other forms vs. controls.

Ntrk2 Expression in the Human Uterus. The truncated form of Ntrk2 was found to be the dominant isoform present whereas the full-length isoform was low to non-detectable (FIG. 6B). A similar analysis was conducted on endometrium from women with endometriosis and the full-length applications/oligoanalyzer/). Primer sequences for BDNF were (Forward: GAGCTGAGCGTGTGTGACAG (SEQ ID NO:9), Reverse: CTTATGAATCGCCAGCCAAT (SEQ ID NO:10)), and for Ntrk2 (For ward: CAATTGTGGTTTGC-CATCTG (SEQ ID NO:11), Reverse: TGCAAAATGCACAGTGAGGT (SEQ ID NO:12)). Primers were ordered from Mobix Laboratory (McMaster University, Hamilton, ON, Canada), and diluted to a working concentration of 10 pmol/ml with DNase/RNase free water. cDNA for 3 animals per group was pooled and used to isolate BDNF and Ntrk2 transcripts. Real-Time PCR was performed in triplicate in a 10 ml reaction volume (2 ml pooled cDNA, 5 ml SYBR Green Master Mix (Qiagen), 1 ml forward primer, 1 ml reverse primer, and 1 ml RNase/DNase free water) using the capillary-based LightCycler (Roche Diagnostics, Laval, QC, Canada). The program was denaturation: 95° C. for 15 min; amplification: 55 cycles: 95° C. for 10 s, 56° C. for 5 s, 72° C. for 20 s; melting curve: 70-95° C. at a rate of 0.1° C. per second. Amplification and melt curves were analyzed for each species using the LightCycler software (Roche Diagnostics). PCR products were collected, and sent for sequencing (Laboratory Services, University of Guelph).

Both primer pairs isolated specific products which were verified by sequencing in all species (human, mouse, rat, and horse).

Example 4

Several studies have indicated that estradiol ($E_2$) treatment alters the expression of Ntrk2 and/or its ligand, BDNF, in neural tissue. To determine if BDNF expression was altered in the uterus, the following study was conducted.

BDNF transcripts were measured in the murine uterus of ovariectomized mice by Real Time PCR and relative expression quantified in mice receiving saline (Control (n=4)), estradiol primed then estradiol (E2 (n=6)), estradiol primed then progesterone (P4 (n=6)), estradiol primed then estradiol+progesterone ($E_2+P_4$ (n=6)), or estradiol primed then saline (Saline (n=4).

| Group | Day 1 | Day 2 | Day 3 | Day 4 | Day 5 | Day 6 | Day 7 | Day 8 | Day 9 |
|---|---|---|---|---|---|---|---|---|---|
| Control | Saline | Saline | Saline | None | None | Saline | Saline | Saline | Saline |
| E2 | $E_2$ | $E_2$ | $E_2$ | None | None | $E_2$ | $E_2$ | $E_2$ | $E_2$ |
| P4 | $E_2$ | $E_2$ | $E_2$ | None | None | $P_4$ | $P_4$ | $P_4$ | $P_4$ |
| E2&P4 | $E_2$ | $E_2$ | $E_2$ | None | None | $E_2 + P_4$ | $E_2 + P_4$ | $E_2 + P_4$ | $E_2 + P_4$ |
| Saline | $E_2$ | $E_2$ | $E_2$ | None | None | Saline | Saline | Saline | Saline |

(FL) variant of Ntrk2 was overexpressed compared to a truncated (T½) variant of Ntrk2vs. controls (FIG. 7).

Example 3—Determination of BDNF and Ntrk2 Expression by PCR

RNA from mouse, rat, human, pig, and horse was reverse transcribed using the iScript cDNA synthesis kit (Bio-Rad), according to kit protocol. PCR primers were designed using human GenBank sequences for BDNF mRNA (NM_001143809.1) and Ntrk2 mRNA (NM_006180.3). Primers were designed against a 300 bp span within the coding region of the gene, and whenever possible were designed to span an intron. Primer3 software (http://frodo.w-i.mit.edu/primer3/) was used for primer design and primers were tested for hairpins, self-dimers, and hetero-dimers using OligoAnalyzer 3.1 (http://www.idtdna.com/analyzer/

BDNF expression was significantly increased in the uterus of ovariectomized mice treated with $E_2$ and progesterone ($P_4$), an effect that was further enhanced by co-treatment with $E_2$ and $P_4$ (FIG. 8).

Example 5—Biomarker Panel for Detecting or Monitoring Endometriosis

Study participants: Women (n=134) undergoing a laparoscopic procedure at McMaster University Medical Centre for chronic pelvic pain were invited to participate in this study. This study was approved by the Hamilton integrated Research Ethics Board, McMaster University (REB #12-083-T). Exclusion criteria included all women unable to consent, those under the age of 18, those who were pregnant, or those with a diagnosis of adenomyosis. All women were asked to consent and complete a questionnaire assessing demographics, menstrual cycle length, date of last menstruation, and pelvic pain. During laparoscopic surgery, women were categorized as a case (n=96) or symptomatic control (n=25) by a gynecological surgeon (NL) with extensive experience in the diagnosis and treatment of endometriosis. The stage of endometriosis was assigned during surgery according to the revised American Society for Reproductive Medicine (rASRM) classification system, as described in *Medicine ASoR: Revised American Society for Reproductive Medicine classification of endometriosis:* 1996. *FertSteril* 1997, 67:817-21. Diagnosis was additionally confirmed through review of pathology reports. Menstrual cycle stage was further confirmed by histopathology.

Participants who received hormone therapies within at least the 3 months before study enrollment were included as a separate subgroup of treated cases (n=39) to determine the effect of ovarian suppression treatment on circulating clinical markers. Thus, there were 57 untreated study participants in the case group.

Sample Collection: Blood samples were collected from the cubital vein into serum and plasma separator tubes by a nurse at McMaster University hospital prior to surgery. Blood was placed on ice, transferred to the laboratory, allowed to clot for 1 hour at 4° C., and centrifuged at 3,000 rpm. Approximately 200 µL of plasma or serum was aliquoted into 1.8 mL cryovials and frozen at −80° C. until required for analysis. Samples were stored in separate aliquots and only thawed once for each assay to avoid repeat freeze/thaw cycles.

Quantification of Circulating Concentrations of Clinical Markers: Samples were thawed at room temperature and concentrations of each protein were quantified in duplicate using commercially available and externally validated quantitative ELISA kits following the manufacturer's protocols. The clinical markers quantified include: brain derived neurotrophic factor (BDNF, Promega, Madison, WI), CA-125, VEGF, IL-1β, IL-6, RANTES, sICAM-1 (R&D Systems, Minneapolis, MN), z-alpha-glycoprotein (ZAG), leptin (Abnova, Walnut, CA), glycodelin (Biosery Diagnostics, Rostock, Germany), and SERPINE2 (Cloud-Clone Corp, Houston, TX). Optical densities were determined for each sample at a wavelength of 450 nm.

The detection limits, and intra- and inter-assay coefficients of variation for each target protein measured were: BDNF (15.6 pg/ml, 2.2% and 8.6%), VEGF (9.0 pg/mL, 5.4% and 7.3%), IL-1β (0.033 pg/mL, <10% and <12%), IL-6 (0.7 pg/mL, 2.6% and 4.5%), RANTES (2.0 pg/mL, 2.4% and 6.5%), ZAG (21 pg/mL, <10% and <15%), glycodelin (6 ng/mL, 8.3% and 4.6%), sICAM-1 (0.096 ng/mL, 4.6% and 5.5%), leptin: (0.2 ng/mL, 5.9% and 5.6%), SERPINE2: (0.135 ng/mL, <10% and <12%), respectively.

Statistical Analysis: The proportions of study participants in each group were compared by Chi-square. Circulating marker concentrations were compared using t-test (cases vs. controls), or one-way ANOVA (comparisons between controls and disease stages) when data was normally distributed. For non-normally distributed data, Mann-Whitney rank sum test and Kruskal-Wallis one-way ANOVA on ranks were used. Statistical analyses were carried out using SigmaStat 3.5 software (Systat Software Inc., Chicago, IL). Data are presented as the mean±SD or median (25%-75% percentiles), as indicated. Results were considered statistically significant for p≤0.05.

To determine the effects of menstrual cycle phase on circulating biomarker concentrations, samples from controls were analyzed according to menstrual stage. If no significant differences were observed for a biomarker in either of these comparisons, subsequent analysis included all controls as one group. Comparisons were then made between all untreated cases and controls, untreated cases stratified by stage of disease (I-II vs. III-IV) and controls, and all cases stratified by treatment (treated vs. untreated) and controls for each biomarker. Receiver operating characteristic (ROC) curves were generated and the area under the curve (AUC) calculated. The sensitivity and specificity for each marker was determined based on an optimal concentration cut-off value.

To evaluate potential benefits of combining clinical markers, Classification and Regression Tree (CART) analysis, a powerful nonparametric statistical procedure for advanced predictive modeling (Predictive Modeler Software Suite version 7.0, Salford Systems, San Diego, CA, USA), was employed. Briefly, multiple potential continuous predictor variables of a binary dependent variable (i.e. endometriosis or control) are inputted with the modeler examining all possible dichotomous splits of subjects based on cut-off values of predictor variables. A decision-tree is created with different splits that best classify subjects (i.e. optimal sensitivity and specificity) with respect to the dependent variable. At the top of the decision-tree, two child nodes are created from a parent node (the "root" node) with subjects having a concentration of a particular biomarker greater than a cut-off value being classified in one node, and subjects having a concentration below a cut-off value for that particular biomarker being classified in the other node. The proportion of cases and controls both above and below the cut-off value are stated in each node. One (or both) of the child nodes then acts as a parent node for another set of child nodes with a different cut-off value of a different biomarker determining how the subject population from the parent node is split. This process continues until terminal nodes are reached, which are mutually exclusive and exhaustive subgroups of the patient population that classify patients as either having the disease (cases=1) or not (controls=0). Sensitivities and specificities are then calculated based on these classifications. Additionally, the tree-growing methodology can be modified to avoid costly type I (false positive) or II (false negative) errors through adjustable misclassification penalties. Through these adjustments, a decision-tree optimized for sensitivity or specificity can be created. This modification was used to create a decision-tree optimized for sensitivity. A biomarker was deemed suitable for inclusion in CART analysis when ROC curves resulted in an AUC≥0.6. The minimum number of subjects in a terminal node was set to n=3.

Results

Patient Characteristics: All women included in this study (134) underwent laparoscopic surgery, from which 106 cases of endometriosis and 28 symptomatic controls where identified. Over all, 13 women were excluded from this study owing to a diagnosis of adenomyosis (cases n=10, controls n=3). The final study population constituted 121 women: 96 cases and 25 controls as shown in Table 1.

TABLE 1

Patient characteristics of women with and without endometriosis.

| Characteristic | Control (25) | Cases (96) | p Value |
|---|---|---|---|
| Age (y), mean ± SD | 34.3 ± 8.3 | 33.6 ± 6.5 | p = 0.722 |
| Stage n (%) | | | NA |
| Minimal 1 | 0 (0) | 8 (8) | |

TABLE 1-continued

Patient characteristics of women with and without endometriosis.

| Characteristic | Control (25) | Cases (96) | p Value |
|---|---|---|---|
| Mild 2 | 0 (0) | 7 (7) | |
| Moderate 3 | 0 (0) | 10 (11) | |
| Severe 4 | 0 (0) | 52 (54) | |
| Not available | 0 (0) | 19 (20) | |
| Current Med n (%) | | | p = 0.012 |
| Hormonal contraceptives | 4 (14) | 28 (27) | |
| Lupron | 3 (11) | 21 (20) | |
| NSAID | 2 (7) | 28 (27) | |
| Narcotic analgesic | 1 (4) | 7 (7) | |
| none/other | 18 (64) | 34 (32) | |
| Menstrual Cycle Stage n (%) | | | |
| Menstrual | 7 (28) | 21 (22) | p = 0.6 |
| Proliferative | 8 (32) | 22 (23) | |
| Secretory | 4 (16) | 22 (23) | |
| Unknown | 6 (24) | 31 (32) | |
| Duration of Bleeding, d Median (25%-75) | 6 (5-7) | 6 (4-7) | p = 0.198 |
| Age at First Menstruation, y Median (25%-75) | 13 (12-14) | 12 (11-13) | p = 0.249 |
| Ethnicity n (%) | | | p = 0.095 |
| Caucasian | 19 (76) | 70 (73) | |
| Asian | 4 (16) | 8 (8) | |
| Black | 0 (0) | 5 (5) | |
| Aboriginal | 1 (4) | 0 | |
| Unknown | 1 (4) | 13 (14) | |
| Occupational Status n (%) | | | p = 0.329 |
| Employed | 19 (76) | 54 (56) | |
| Unemployed | 1 (4) | 11 (11) | |
| Other | 1 (4) | 5 (5) | |
| Unknown | 4 (16) | 26 (27) | |
| Smoking Status | | | p = 0.496 |
| Yes | 5 (40) | 14 (15) | |
| No | 20 (80) | 77 (80) | |
| Unknown | 0 | 4 (4) | |

SD: standard deviation,
y: years,
d: days

The current study population consisted of cases with stage I (n=8), stage II (n=7), stage III (n=10), and stage IV (n=52). Disease stage information was unavailable for n=19 cases. Only current medication use differed significantly (p=0.012) between cases and controls. Of the 96 confirmed cases of endometriosis, n=39 (41%) received hormonal treatment within three months prior to surgery, while n=57 (59%) were untreated. Of the 25 controls, n=7 (28%) reported use of OCP and non-steroidal anti-inflammatory drugs (NSAIDs) while n=18 (72%) denied medication use. The average age, ethnicity, occupational status, smoking status, age at first menstruation, median duration of bleeding, and menstrual cycle stage showed no significant differences between cases and controls.

Effect of Treatment on Peripheral Biomarkers: No significant differences were found when comparing treated and untreated controls for any of the biomarkers tested. Similarly, there were no differences in concentrations of any marker over the course of the menstrual cycle. Therefore, data from these groups were combined into a single control group.

Biomarkers and Endometriosis: To determine the effect of endometriosis on circulating biomarker concentrations, marker concentrations were compared in samples from untreated cases (n=57) and all controls (n=25). Only glycodelin (p=0.041) and BDNF (p=0.0008) showed a significant difference between untreated cases and controls (Table 2). The concentrations of ZAG approached but did not reach statistical significance (p=0.086). ROC curves were generated for glycodelin, BDNF, ZAG, and CA-125 (FIG. 11A-D). The AUC for BDNF 0.73 (p<0.001) and glycodelin 0.70 (p=0.040) were statistically significant whereas the AUC for ZAG 0.66 (p=0.085) and CA-125 0.47 (p=0.622) failed to reach significance (FIG. 11E). The sensitivity and specificity for each marker was determined at cut-off values chosen to maximize marker accuracy (Table 2). Using a cut-off value of 944.6 pg/mL for BDNF yielded a sensitivity of 68.3% (CI 55.0-79.7) and a specificity of 80.8% (CI 60.7-93.5). For glycodelin, using a cut-off value of 19.8 ng/ml produced a sensitivity of 77.1% (CI 59.9-89.6) and a specificity of 58.3% (CI 27.7-84.8). At a cut-off value of 91.6 pg/ml, ZAG achieved a sensitivity of 47.2% (CI 33.3-61.4) and a specificity of 100% (CI 73.5-100). At a cut-off value of 14.9 U/mL CA125 achieved a sensitivity of 22.2% (CI 12.0-35.6) and a specificity of 100% (CI 86.8-100).

TABLE 2

| | Concentrations of clinical markers in women with endometriosis vs. a control population. | | |
|---|---|---|---|
| Marker | Control (n = 25) | Case (n = 96) | p value |
| VEGF (pg/ml) | 269.6 (96.6-350.1) | 212.8 (124.1-339.2) | 0.98 |
| BDNF (pg/ml) | 629.7 (338.0-917.9) | 1108 (663.8-1742) | 0.0008 |
| CA-125 (U/ml) | 7.21 (5.58-10.71) | 7.30 (3.61-13.32) | 0.63 |
| IL-1β (pg/ml) | 0.058 (0.033-0.10) | 0.052 (0.037-0.079) | 0.64 |
| IL-6 (pg/ml) | 0.35 (0.06-1.41) | 0.10 (0.06-0.80) | 0.58 |
| RANTES (ng/ml) | 33.4 (21.4-62.1) | 37.4 (19.9-65.5) | 0.57 |
| sICAM (ng/ml) | 208.4 ± 46.0 | 218.1 ± 51.0 | 0.44 |
| Glycodelin(ng/ml) | 12.3 (5.2-31.4) | 47.1 (21.6-92.2) | <0.001 |
| ZAG (pg/ml) | 50.4 (41.7-64.9) | 73.7 (46.6-115.3) | 0.085 |
| Leptin (ng/ml) | 13.5 (8.7-22.7) | 16.4 (8.3-25.2) | 0.81 |
| SERPIN2 (ng/ml) | 16.1 (13.4-24.8) | 17.0 (14.3-20.7) | 0.81 |

The data are presented as the median ($25^{th}$-$75^{th}$ percentile) or the mean ± SD for normally distributed data.

CART Analysis: Clinical markers with an ROC value greater than or equal to 0.60 were included in the analyses using CART software (Salford Systems). The only markers investigated able to satisfy this criterion were BDNF (AUC=0.73), glycodelin (AUC=0.70) and ZAG (AUC=0.66). CART analysis revealed that BDNF, glycodelin, and ZAG were able to form a decision-tree with a sensitivity of 76.9% and a specificity of 93.3% for the diagnosis of endometriosis (FIG. 12). Given the high cost of misdiagnosing a patient with endometriosis as a control (false negative), the CART methodology was modified to create a decision-tree optimized for sensitivity. This analysis produced a decision-tree able to diagnose disease with a sensitivity of 89.2% and a specificity of 70.0% (FIG. 13).

Markers and Stage of Disease: The effect of disease stage on peripheral marker was determined through comparing biomarker concentrations of untreated cases with stage I-II disease (n=8), untreated cases with stage III-IV disease (n=44), and controls (n=25). BDNF and glycodelin were the only markers to show significant variation in concentrations between stages of disease. Median BDNF concentrations were significantly (p=0.0045) higher in stage I-II vs. III-IV stage disease (1147 vs. 1087 pg/ml) and controls (629.7 pg/ml), suggesting that BDNF concentrations are higher in early stage active disease (stage I-II). There was less difference in median glycodelin concentrations (p=0.41) between women with stage I-II disease and the control group (21.6 vs. 12.3 ng/ml), respectively, than between women with stage III-IV disease and the control group. Thus, median glycodelin concentrations were significantly (p=0.027) lower in stage I-II vs stage III-IV disease (21.6 vs. 61.5 ng/ml), suggesting that glycodelin concentrations rise with disease severity.

Markers and Hormonal Treatment: The effect of hormonal treatment on circulating levels of putative biomarkers in patients with endometriosis was assessed. Of the clinical markers quantified, only BDNF (p<0.05) and glycodelin (p<0.001) demonstrated a significant difference between treated and untreated cases. BDNF concentrations in the plasma were significantly lower in treated than untreated cases (729.1 vs. 1097 pg/ml). Similarly, median glycodelin concentrations were significantly lower in treated vs. untreated cases (8.37 vs. 47.1 ng/ml).

Discussion

In the present study, circulating concentrations of single biomarkers alone and in combination were evaluated for the diagnosis of endometriosis in women undergoing laparoscopy for pelvic pain. The results revealed that circulating concentrations of BDNF and glycodelin were significantly higher in women with endometriosis compared to disease free controls. Analysis by stage of disease revealed that the circulating concentrations of BDNF were higher in stage I-II disease compared to stages whereas the reverse was true for glycodelin. Taken together these results suggest that BDNF may be a better indicator of active disease, whereas glycodelin has value in identifying more advanced stages of endometriosis. CART analysis showed that the combination of BDNF, glycodelin and ZAG yielded a sensitivity and specificity of 89.2% and 70%, respectively.

In view of the lengthy delays in diagnosis and the invasive nature of laparoscopy which itself is not perfect for the diagnosis of endometriosis, these biomarkers could provide evidence in support of clinical judgment for the empirical initiation of approved treatments for endometriosis, thus allowing for quicker patient access to effective medical treatment and management. Further, this panel of markers may lead to the avoidance of unnecessary diagnostic laparoscopy in those that do not have endometriosis. Results of the present study also revealed that both BDNF and glycodelin concentrations were significantly lower in treated vs. untreated cases. For example, both BDNF and glycodelin had lower concentrations in women with endometriosis who were treated with ovarian suppressing agents and, thus, these markers have value as indicators of treatment response, and thus, may replace laparoscopy for this purpose.

BDNF, glycodelin, and ZAG produced acceptable ROCs for further study. Combining these three clinical markers in CART analysis yielded a sensitivity and specificity of 76.9% and 93.3%, respectively. The positive predictive value (PPV) of this test was 96.2% with a negative predictive value (NPV) of 65.1%. Optimizing the CART analysis to favor sensitivity over specificity we obtained adjusted sensitivity and specificity values of 89.2% and 70.0%, respectively with a PPV of 86.6% and NPV of 75%.

In summary, BDNF and glycodelin were found to be superior to both emerging (SERPINE2 and ZAG) and classical markers (CA-125, ZAG, VEGF, IL-6, IL-1β, RANTES, sICAM-1, and leptin) as single non-invasive markers for the diagnosis of endometriosis in the present study population. Furthermore, combination of BDNF, glycodelin and ZAG in a panel produced a sensitivity and specificity that was superior to either marker alone. Both circulating BDNF and glycodelin concentrations have been positively associated with pain and their concentrations declined with treatment. Therefore, the present clinical markers can be used to aid in clinical decisions to initiate effective medical treatment and management of women with endometriosis, and BDNF and/or glycodelin can be used to monitor patient response to treatment.

Example 6—Device for Detecting or Monitoring Endometriosis

Materials: BDNF antigen and anti-BDNF antibody, gold chloride (HAuCl), 50% (w/w) glutaraldehyde, Potassium ferricyanide (FiCN, 99.0%), and cystamine were purchased from Sigma-Aldrich. Potassium chloride (KCl, ≥99.0%), phosphate buffer solution (PBS, 1.0M, pH 7.4) was purchased from Anachemia (Rouses Point, NY). Pot Sulfuric acid (H2504, 98%), 2-propanol (99.5%) were purchased from Caledon Laboratories (Georgetown, Ontario). Ethanol was purchased from Commercial Alcohols (Brampton, ON). Immobilized TCEP Disulfide Reducing Resin was purchased from Thermo Scientific (Rockford, IL). Tris-(hydroxymethyl)aminomethane (tris, ≥99.9%) was purchased from BioShop Canada (Burlington, ON). The hydrogen peroxide ($H_2O_2$) was purchased from Caledon. Milli-Q grade ultrapure water (18.2 MΩ·cm) was used to prepare all solutions and for all washing steps.

Device Fabrication: Two sets of devices were created: (1) electrochemistry on a linear surface (planar device); and (2) on a porous device (craft cut and (3-aminopropyl) triethoxysilane (APTES) solution-treated polymer). The first set of electrodes (CH Instruments, Austin, Texas) were cleaned by polishing followed by sonication in ethanol for two 5 minute intervals, DI water for 30 seconds, and then air dried. For the second set, a clean commercially available polysterene (PS) substrate was plasma treated and incubated in a 10% APTES. The APTES acts as a self-assembled monolayer with amine affinity for gold (Au). The substrate was covered with a self-adhesive vinyl sheet. A Robo Pro CE5000-40-CRP vinyl cutter equipped with a CB09UA supersteel blade was used with Adobe Illustrator [v.16.0.3] CAD modeling software to create the desired shapes. The masked surface is attached to the substrate and incubated in Au nanoparticle (NP) solution overnight to form a seed layer. Electroless deposition was performed on the planted seed layer by immersion into chloroauric acid (HAuCl4) followed by an injection of hydrogen peroxide ($H_2O_2$) for 2 minutes and then the Au-treated substrate was rinsed with water. Following the electroless Au deposition process, the vinyl mask was removed with tweezers and rinsed with DI water. The devices were heated for 3 minutes at 160° C. in order to be shrunk and rinsed again.

Deposition of Immunosensor Probes for Protein Detection: For both planar and porous electrode experiments, a self-assembled monolayer (SAM) was created as the primary linker of the detection device by applying a 2 M cystamine solution at room temperature overnight. An optimization step was performed to determine the effectiveness of increasing concentrations of cystamine. A 2 M cystamine solution yielded the best results and thus was used for all subsequent procedures. Before applying the cystamine solution, a 1 hour reduction was performed with TCEP disulfide reduction solution to lyse the sulfide bond in the cystamine molecule, which is required for the immobilization of the secondary linker. After being rinsed with DI water, the SAM was introduced to the secondary linker, 2.5% glutaraldehyde in water, for 1 hour and rinsed again.

To test the ability of the devices to detect BDNF, 10 ug/mL anti-BDNF-antibody in phosphate buffered saline (PBS) was incubated with the device at room temperature for 1 hour. After being washed with PBS twice for 5 minutes, 5% (w/v) bovine serum albumin in PBS was applied to the sensor surface in order the block the unreacted aldehyde groups so that they do not interfere with the electrochemical signal. The sensors were washed 3 times with PBS. Increasing concentrations of BDNF (0.5, 1, and 2 ng/ml) in PBS were applied to the immunosensors for 40 minutes at 37° C. and washed with PBS and water before electrochemical measurements were assessed.

Electrochemical Measurements: All electrochemical experiments were performed using a CH1 660D potentiostat (CH Instruments, Austin, Texas) connected to a 3-electrode arrangement consisting of a reference electrode Ag/AfCl (1.0 M KCl) and a counter electrode platinum wire. The porous working electrode was created with three 2×2 mm square electrodes per device connected with thin gold lines to a contact pad which is attached to metal clip. The planar working electrode is already customized with a built in clip. The surface areas of the porous and planar electrodes were calculated using cyclic voltammetry (CV) in a 0.05 M H2SO4 solution by integrating the Au reduction peaks of the cyclic Voltammogram and dividing that reduction charge by the surface charge density. The surface charge density of the Au monolayer was experimentally determined to be 386 uC/cm.

Protein Detection and SEM Images: Electrochemical signals were measured in an electrochemical solution containing 2.5 mM $K_3[Fe(CN)_6]$, 2.5 mM $K_2[Fe(CN)_6]$, 0.1 M KCl, and 10 mM phosphate buffer solution (PBS). Cyclic voltammetry (CV) was obtained with a scan rate of 100 mV/s, and differential pulse voltammetry (DPV) signals were obtained with a potential step of 5 mV, pulse amplitude of 50 mV, pulse with 50 ms, and a pulse period of 100 ms (as described by Woo et al. 2014). Signal percentage changes corresponding to target protein binding to the antibody were determined by calculating the difference between the average current before and after adding the target analyte. Three differential pulse voltammograms were performed per concentration to ensure accuracy of the reading. SEM images of planar and porous gold electrodes were obtained using a JEOL JSM-70005 scanning electron microscope with an accelerating voltage of 2 kV, working distance of 6 mm, and low probe current.

Clinical samples: To demonstrate the ability of the device to detect plasma BDNF concentrations and discriminate between cases and controls, plasma samples were collected and utilized. Briefly, five samples that had circulating concentrations of BDNF above 1.0 ng/ml (cases) and five samples in which the concentrations of BDNF were previously shown to be less than 0.6 ng/ml (controls) were randomly selected from the archive and coded. Each sample was tested in triplicate by a study team member (MB) blinded to prior study results. Once all the scans were completed the code was broken and results assigned to the case or control group based on results from the original study and data from the current study.

Results and Discussion

The process for making the porous APTES-treated polystyrene-based electrode is shown in FIG. 16. The template for the seed layer was designed using CAD program and self-adhesive vinyl was cut and placed as a mask. A seed layer of a 12 nm gold nanoparticles was then used to fill the pores with a gold film. The gold film was then activated with the addition of hydrogen peroxide ($H_2O_2$) and gold chloride ($HAuCl_4$). This electroless method does not require photolithography, which is advantageous for cost efficient multiplexing of chips on a single substrate. The chips were then shrunk thermally in the oven at 160 degrees C. for 3 minutes. It is the shrinking process that causes height variations in the electrode surface, therefore creating pores. The porous electrodes demonstrated an increased limit of detection compared to the planar electrodes because it increases surface area, and thus, sensitivity of the biosensors through its textured surface (see FIG. 17).

In order to functionalize the electrodes as immunosensors, a self-assembled monolayer of cystamine was immobilized on the gold surface through a thiol bond because thiols have a high affinity for metals. Additionally, its amine functional group provides the ability for the bifunctional linker, glutaraldehyde, to attach. Gluteraldehyde provides a ketone functional group that is capable of attaching a biomarker-specific reactant, such as an antibody, for detecting a target analyte (e.g. BDNF). Adding an aqueous solution of each chemical over the chips forms these linkers. Moreover, the anti-BDNF monoclonal antibody is the probe on the electrode surface that will specifically attach to its target analyte, BDNF protein. Antibodies circulate in plasma as an immunological response system that detect and attach to foreign entities. The variable region of the antibody polypeptide chain recognize and attach to its corresponding antigen, BDNF. Monoclonal antibodies are ideal because they are highly specific and are exclusive to one epitope.

In order to correlate the concentration of BDNF protein attached to the antibody probes, a voltage is applied to generate an electrochemical signal from the working electrode, which is comprised of the antibody probes. The working electrode is surrounded by a redox reporter, $[Fe(CN)_6]^{3-/4-}$, which produces a faradaic current through interfacial electron transfer. A comparison of the electrochemical signal with and without protein analyte was performed and illustrated a decrease in signal in the presence of protein since the protein blocks the redox reporter from accessing the electrode surface. Less electron transfer equals less current produced, therefore a smaller current signal is measured. These signals are measured using a differential pulse voltammogram, which illustrated the reduction peak as interfacial electron transfer occurs (FIG. 19). Using known concentrations of BDNF protein in PBS (1×), the mean difference in current change was calculated for increasing concentrations (FIG. 18). This information is used to determine BDNF concentrations in blood samples by calibrating the detection system with the known concentration standards between 1 ng/mL and 4 ng/mL.

Conclusion

Through the use of a three electrode system, deciphering positive protein-antibody binding correlates to the positive identification of disease progression, specifically, the amount of adhesions in an endometriosis patient. Smooth or porous electrodes may be used. Alteration of the electrode surface morphology has demonstrated an increase in sensitivity regarding a probe vs. BDNF protein signal change both in PBS and patient plasma. In either case, electrodes have been successfully utilized to detect a target analyte, such as BDNF, and may be utilized to detect other endometriosis biomarkers as well, either separately or in a multiplexed platform.

The invention claimed is:

1. A method of diagnosing endometriosis in a human, the method comprising:

detecting an expression level of circulating brain-derived neurotrophic factor (BDNF) in a biological fluid sample taken from the human;

comparing the circulating BDNF expression level to a BDNF control level to determine if the circulating BDNF level is elevated as compared to the control level, wherein the control level is an expression level of BDNF in a human without endometriosis;

diagnosing the human with endometriosis when the circulating BDNF expression level is elevated by at least 10% as compared to the BDNF control level; and further diagnosing a stage of the endometriosis if present, wherein elevation of the circulating BDNF expression level by 30% to 50% as compared to the BDNF control level is indicative of stage 1 or stage 2 endometriosis.

2. The method of claim 1, wherein the biological sample is selected from the group consisting of blood, serum, plasma, urine and peritoneal fluid.

3. The method of claim 1, further comprising determining the expression level of cancer antigen 125 (CA-125) in the biological sample from the human and comparing the CA-125 expression level to a CA-125 control level, wherein the control level is an expression level of CA-125 in a human without endometriosis.

4. The method of claim 1, wherein the control level of BDNF is 100-500 μg/ml.

5. The method of claim 1, wherein the BDNF is total plasma BDNF.

6. The method of claim 1, wherein the determining step comprises contacting the biological fluid sample with an anti-BDNF antibody and detecting binding between the BDNF from the biological fluid sample and the anti-BDNF antibody, wherein the anti-BDNF antibody is selected from the group consisting of a polyclonal antibody, a monoclonal antibody, and an antigen-binding fragment.

7. A method of diagnosing endometriosis in a human with pelvic pain, the method comprising:

detecting an expression level of circulating brain-derived neurotrophic factor (BDNF) in a biological fluid sample taken from the human with pelvic pain;

comparing the circulating BDNF expression level to a BDNF control level to determine if the circulating BDNF level is elevated as compared to the control level, wherein the control level is an expression level of BDNF in a human without endometriosis; and diagnosing the human with endometriosis when the circulating BDNF expression level is elevated as compared to the BDNF control level.

8. The method of claim 7, wherein the biological sample is selected from the group consisting of blood, serum, plasma, urine and peritoneal fluid.

9. The method of claim 7, wherein the determining step comprises contacting the biological fluid sample with an anti-BDNF antibody and detecting binding between the BDNF from the biological fluid sample and the anti-BDNF antibody, wherein the anti-BDNF antibody is selected from the group consisting of a polyclonal antibody, a monoclonal antibody, and an antigen-binding fragment.

10. The method of claim 7, further comprising determining the expression level of cancer antigen CA-125 in the biological sample from the human with pelvic pain and comparing the CA-125 expression level to a CA-125 control level, wherein the control level is an expression level of CA-125 in a human without endometriosis.

11. A method of diagnosing endometriosis in a human, the method comprising:

detecting the expression level of circulating brain-derived neurotrophic factor (BDNF) and cancer antigen 125 (CA-125) in a biological fluid sample taken from the human;

comparing the circulating expression levels of BDNF and CA-125 to control levels of BDNF and CA-125 to determine if the circulating BDNF and CA-125 levels are elevated as compared to the control levels, wherein the control levels are expression levels of each of BDNF and CA-125 in a human without endometriosis; and diagnosing the human with endometriosis when one or both of the circulating BDNF and CA-125 expression levels are elevated as compared to the BDNF and CA-125 control levels.

12. The method of claim 11, further comprising:

diagnosing the human with endometriosis when the circulating BDNF expression level is elevated by at least 10% as compared to the BDNF control level; and further diagnosing a stage of the endometriosis, wherein elevation of the circulating BDNF expression level by 30% to 50% as compared to the BDNF control level is indicative of stage 1 or stage 2 endometriosis.

13. The method of claim 11, wherein the biological sample is selected from the group consisting of blood, serum, plasma, urine and peritoneal fluid.

14. The method of claim 11, wherein the determining step comprises contacting the biological fluid sample with an anti-BDNF antibody and an anti-CA-125 antibody, and detecting binding between the BDNF and the anti-BDNF antibody and between the CA-125 from the biological fluid sample and the anti-CA-125 antibody, wherein the anti-BDNF and anti-CA-125 antibodies are selected from the group consisting of a polyclonal antibody, a monoclonal antibody, and an antigen-binding fragment.

15. The method of claim 11, wherein the human has pelvic pain.

* * * * *